(12) United States Patent
DeMarco

(10) Patent No.: US 7,318,900 B2
(45) Date of Patent: Jan. 15, 2008

(54) CHROMATOGRAPHY SYSTEM AND METHOD

(75) Inventor: Nicholas DeMarco, Burlington, WI (US)

(73) Assignee: Varian, Inc., Palo Alto, CA (US)

( * ) Notice: Subject to any disclaimer, the term of this patent is extended or adjusted under 35 U.S.C. 154(b) by 306 days.

(21) Appl. No.: 11/084,741

(22) Filed: Feb. 25, 2005

(65) Prior Publication Data
US 2006/0027490 A1 Feb. 9, 2006

Related U.S. Application Data

(60) Provisional application No. 60/547,613, filed on Feb. 25, 2004.

(51) Int. Cl.
*B01D 15/08* (2006.01)
(52) U.S. Cl. ............... 210/656; 210/143; 210/198.2
(58) Field of Classification Search ............ 210/656, 210/635, 659, 143, 198.2; 422/70; 73/61.52; 702/22, 30, 32
See application file for complete search history.

(56) References Cited

U.S. PATENT DOCUMENTS

| | | | | |
|---|---|---|---|---|
| 5,670,054 | A * | 9/1997 | Kibbey et al. | 210/656 |
| 6,456,955 | B1 * | 9/2002 | Andrews et al. | 702/104 |
| 6,767,467 | B2 * | 7/2004 | Fischer et al. | 210/659 |
| 7,138,051 | B2 * | 11/2006 | De Lamotte | 210/198.2 |
| 2002/0121468 | A1 * | 9/2002 | Fischer et al. | 210/198.2 |
| 2002/0166816 | A1 * | 11/2002 | Allen et al. | 210/656 |
| 2005/0082228 | A1 * | 4/2005 | De Lamotte | 210/656 |
| 2006/0093521 | A1 * | 5/2006 | Swartz et al. | 422/70 |

OTHER PUBLICATIONS

ISCO, Inc.; "COMBIFLASH® Separation Systems;" Brochure #2111DSLC; www.isco.com; U.S.A; Sep. 1998; 2 pages.

* cited by examiner

*Primary Examiner*—Ernest G. Therkorn
(74) *Attorney, Agent, or Firm*—Michael Best & Friedrich LLP

(57) ABSTRACT

A chromatography system and method for analyzing a sample of interest. The chromatography system can include a housing, a cartridge holder coupled to the housing and formed to hold a chromatography cartridge containing a stationary phase, a collection vessel stand holder coupled to the housing and formed to hold a collection vessel stand, and a pump coupled to the housing. A fluid path can be coupled to the housing and can connect the pump to the cartridge holder to direct a mobile phase from the pump to the cartridge holder and can further connect the cartridge holder to the collection vessel stand holder to direct the mobile phase from the cartridge holder to the collection vessel stand holder. The chromatography system can further include a detector positioned along the fluid path between the cartridge holder and the collection vessel stand holder, and a controller integrally coupled to the housing.

6 Claims, 23 Drawing Sheets

CHROMATOGRAPHY SYSTEM AND METHOD

RELATED APPLICATIONS

Priority is hereby claimed to U.S. Provisional Patent Application No. 60/547,613, filed Feb. 25, 2004, the entire contents of which are incorporated herein by reference.

BACKGROUND

The present invention relates generally to a chromatography system and method, and particularly, to a liquid chromatography system and method, and more particularly, to a flash chromatography system. Chromatography is used to analyze the constituents, or fractions, of a sample of interest, and, in some cases, to collect each of the fractions of the sample of interest separately for further analysis or use. Chromatography generally relates to any of a variety of techniques used to separate complex mixtures based on the differential affinities of the fractions of the sample for a mobile phase with which the sample flows, and a stationary phase through which the sample passes.

Generally, liquid chromatography includes a stationary phase that includes a finely powdered solid adsorbent packed into a chromatography cartridge or column, and the mobile phase includes one or more eluting solvents that are moved through the cartridge by a pump. The sample to be analyzed by liquid chromatography is injected into the cartridge and monitored by a detector. The detector provides identification and/or differentiation of the fractions as the fractions elute from the cartridge. In general, flash chromatography includes a cartridge (in some cases, a disposable cartridge) filled with the stationary phase (e.g., silica gel), and the sample to be separated is placed on top of the stationary phase. The cartridge is filled with an isocratic or gradient solvent which, with the help of pressure, enables the sample to run through the cartridge and become separated. Generally, liquid chromatography, and particularly, flash chromatography can be used for a variety of applications, including, but not limited to, drug discovery, sample clean-up, and natural product purification, among others.

SUMMARY

Some embodiments of the present invention provide a chromatography system for analyzing a sample of interest, and the sample including fractions. The chromatography system can include a housing; a cartridge holder coupled to the housing and formed to hold a chromatography cartridge containing a stationary phase; a collection vessel stand holder coupled to the housing and formed to hold a collection vessel stand; a fraction collector coupled to the housing, the fraction collector selectively dispensing fractions to the collection vessel stand holder; a pump coupled to the housing; a fluid path coupled to the housing and connecting the pump to the cartridge holder to direct a mobile phase from the pump to the cartridge holder and connecting the cartridge holder to the collection vessel stand holder to direct the mobile phase from the cartridge holder to the collection vessel stand holder; a detector positioned along the fluid path between the cartridge holder and the collection vessel stand holder; and a controller integrally coupled to the housing, the controller controlling the pump and receiving data from the detector.

Other features and aspects of the invention will become apparent by consideration of the detailed description, accompanying drawings, and claims.

DETAILED DESCRIPTION

Figure 1:
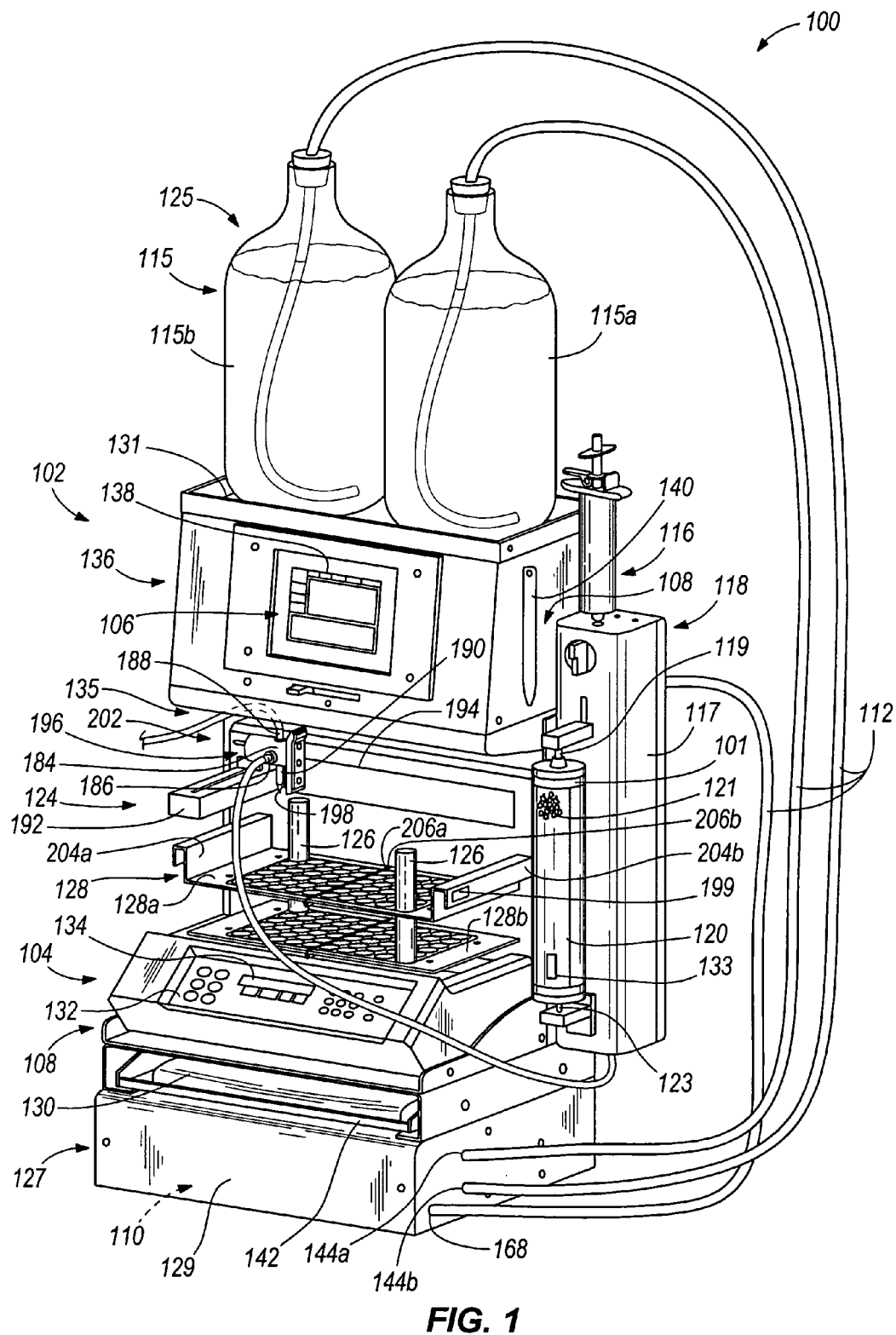
FIG. 1 is a front perspective view of a chromatography system according to one embodiment of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

FIGS. 1-6 illustrate a chromatography system 100 according to one embodiment of the present invention. The chromatography system 100 can be used to detect and separate a sample 101 into its constituents, or fractions. The chromatography system 100 includes a housing 102; a controller 104 with chromatography programming software having a graphical user interface 106; a user interface 108 to allow a user to control various aspects of the system 100; a pump assembly 110 including a pump 114 for moving a mobile phase comprising one or more solvents 115 through a fluid path 112 in the chromatography system 100, and, in some embodiments, a mixing valve 113 for mixing the one or more solvents 115; a sample injector 116; a cartridge holder 118 for holding a chromatography cartridge 120 into which the sample 101 will be injected and through which the sample 101 will pass to be separated; a detector 122 for detecting the fractions of the sample 101; and a fraction collector 124 for ejecting fractions of the sample 101, or the entire sample 101, from the chromatography system 100 into one or more collection vessels 126. In some embodiments, the collection vessels 126 are positioned in one or more collection vessel stands 128. The collection vessels 126 can include a variety of containers, including, without limitation, at least one of test tubes 126, as shown in FIGS. 1-6, arranged in one or more test tube racks 128, micro plates, micro vials, scintillation vials, etc.

As used herein and in the appended claims, the term "fluid path" 112 refers collectively to those areas in the chromatography system 100 through which fluid passes. The "fluid path" 112 can include an entire path followed by fluid through the chromatography system 100 or can refer to a portion of that path.

As used herein and in the appended claims, the terms "upstream" and "downstream" refer to the direction of fluid movement in the chromatography system 100. That is, the term "upstream" is used to describe any location, element or process that occurs prior to the point or area being referred to relative to the direction of fluid movement in the chromatography system 100, whereas the term "downstream" is used to describe any location, element or process that occurs subsequent to the point or area of reference with respect to fluid movement in the chromatography system 100.

In general, the sample 101 can be loaded directly into an inlet 119 of the cartridge 120, or the sample 101 can be loaded into the sample injector 116 to be dissolved (e.g., in a stronger solvent to reduce sample viscosity), and then injected into the inlet 119 of the cartridge 120. After the sample 101 has been added to the cartridge 120, the sample 101 interacts with the mobile phase of the system 100 and a stationary phase 121 contained within the cartridge 120. The mobile phase and the sample 101 are moved by the pump 114 through the cartridge 120 at a particular flow rate, or programmed sequence of flow rates. Based on the varying affinities of the fractions of the sample 101 for the solvents 115 and the stationary phase 121, the fractions of the sample 101 will pass through the stationary phase 121 at different flow rates, and thus, elute from an outlet 123 of the cartridge 120 at different times. Each fraction will then flow from the cartridge 120 to the detector 122 positioned downstream from the cartridge 120 in the fluid path 112, and to the fraction collector 124 to be expelled into one or more test tubes 126.

Figure 7:
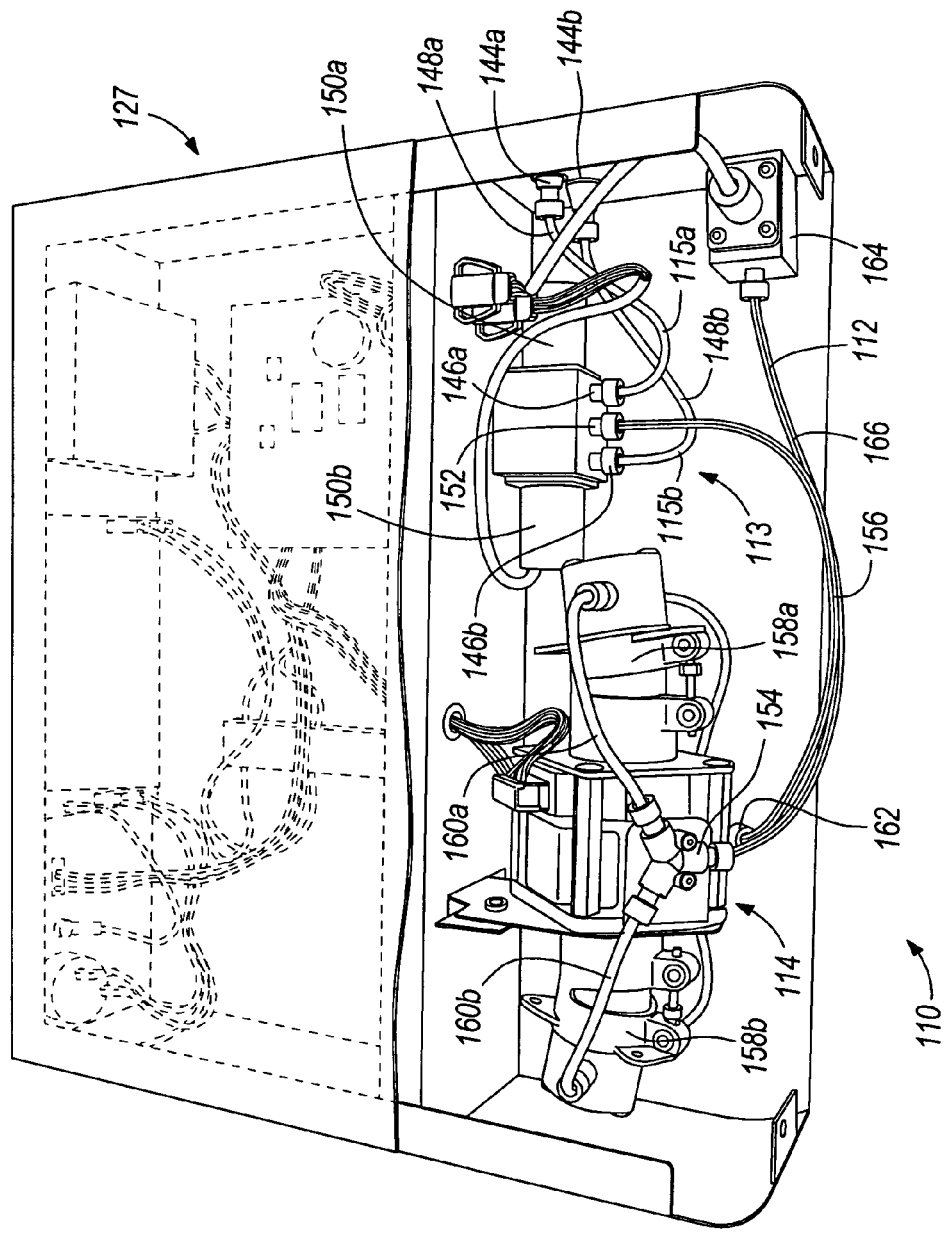
FIG. 7 is a perspective view of a pump assembly according to one embodiment of the present invention.

The housing 102 of the illustrated embodiment is formed of several portions that each house and/or support the various components of the system 100. In some embodiments, the portions of the housing 102 are integrally formed, and the housing 102 is a unitary body. In some embodiments, the portions of the housing 102 are each formed of different parts. For example, in the embodiment illustrated in FIGS. 1-6, the housing 102 is formed of separate parts that are coupled together in a stacked configuration to position the various components of the system 100 in a substantially vertical arrangement. The vertical arrangement of the system 100 creates a relatively compact system 100 that requires a relatively minimal amount of surface area or workspace on a desk, table or lab bench. In addition, the housing 102 allows the components of the system 100 to be positioned in relatively close proximity to one another and to be coupled together to form an integrated chromatography system 100. The integrated chromatography system 100 includes substantially all of the necessary components and devices to perform chromatography, and thus allows for facile installation, set-up and use. In addition, the integrated chromatography system 100 is sized and configured such that substantially the entire chromatography system 100 can be positioned on a lab bench, inside a chemical hood, and the like. The housing 102, or portions thereof, can also be used to protect or conceal (e.g., for aesthetic purposes) various portions of the chromatography system 100. For example, in some embodiments, as shown in FIG. 7, the pump assembly 110 is positioned in a base portion 127 of the housing 102, and is concealed from view by a front plate 129, as shown in FIGS. 1-6.

The housing 102 illustrated in FIGS. 1-6 is shown by way of example only, and it should be understood that other housing configurations and designs can be used to form a relatively compact and integrated chromatography system 100. In addition, it should be understood that the housing 102 can instead be formed of a unitary body. Furthermore, the organization and arrangement of the components of the chromatography system 100 is shown by way of example only, and a variety of other arrangements of the components of the chromatography system 100 can be used to form the integrated chromatography system 100, without departing from the spirit and scope of the present invention.

The controller 104 is internal to the chromatography system 100, and is integral with the chromatography system 100 to eliminate the need for an independent, external personal computer. The controller 104 controls various aspects of the chromatography process. In some embodiments, the controller 104 of the chromatography system 100 is microprocessor-based and is adapted to allow the user to interact with and manipulate the components of the chromatography system 100 to perform a chromatography analysis of the sample 101 of interest. For example, in the embodiment illustrated in FIGS. 1-6, the controller 104 includes computer control hardware with an embedded Intel® Strong ARM 206 MHz RISC processor and a MICROSOFT® Windows CE™-based operating system, such as INTELLIPEAK™ chromatography programming software, available from Analogix, Inc., Burlington, Wis. In other embodiments, the controller 104 can be any programmable or non-programmable electronic system, and need not necessarily be microprocessor-based. The controller 104 can include any combination of hardware and/or software components. By way of example only, the controller 104 can include any number of discrete logic elements coupled together to perform the same function as described above. Still other types of electronic controllers capable of performing this function are possible, would be readily recognized by those skilled in the art, and fall within the spirit and scope of the present invention.

In some embodiments, as shown in the embodiment illustrated in FIGS. 1-6, the controller 104 includes standard personal computer hardware and software. For example, in the embodiment illustrated in FIGS. 1-6, the controller 104 includes MICROSOFT® Windows® CE desktop software. The controller 104 can be connected to one or more external controllers (e.g., personal computers) directly or via a network (e.g., a local area network (LAN) or the internet) for data transfer. For example, the controller 104 can be connected to the internet wirelessly or via an Ethernet connection for data transfer.

The controller 104 can also include a variety of standard input jacks, including a universal serial bus (USB), which can allow a variety of external devices to be connected to the controller 104. For example, memory storage devices can be connected to the controller 104 via a USB connection for file transfer. The controller 104 can include a variety of standard programs (e.g., MICROSOFT® EXCEL™ spreadsheet program) for data storage and analysis, word processing, and the like. The controller 104 can further include a variety of drive devices for file storage and transfer, including, without limitation, at least one of a floppy disk drive, a CD-ROM drive, a DVD-ROM drive, a CD-R drive, a DVD-R drive, a CD-RW drive, a zip drive, and the like. In some embodiments, the controller 104 can include a compact flash memory drive device. In such embodiments, a user can store his/her settings, preferences, and/or chromatography data and results on a flash memory card to allow the user to essentially be "identified" by the controller 104, and for the chromatography system to be customized to each user.

The controller 104 can include chromatography software having a graphical user interface 106 to allow a user to interact with the controller 104 to manipulate and control the chromatography system 100. The graphical user interface allows a user to control a variety of aspects of a chromatography run, including without limitation, changing parameters of a chromatography run, determining a mode of reporting chromatography results, determining a layout or format of reporting a chromatogram or other chromatography results, and analyzing chromatography results. The details of the chromatography software and the graphical user interface 106 will be described in greater detail below.

The controller 104 can be connected to the user interface 108. The user interface 108 can include a variety of devices, including, without limitation, one or more of the following: a keyboard 130, a mouse (not shown), a joystick (not shown), a touchpad 132 with a liquid crystal display (LCD) screen 134, and a monitor 136 for displaying the graphical user interface 106 and having a touch screen 138 (operated by a stylus 140 or a user's fingertip), and the like. In some embodiments, as shown in FIG. 1, the keyboard 130 can be positioned on a keyboard tray 142 that can be coupled to and movable with respect to the housing 102. The keyboard tray 142 can be positioned within a recess of the housing 102 to allow the keyboard 142 to be stowed away when not in use, thereby contributing to the compact configuration of the integrated chromatography system 100.

The cartridge holder 118 is coupled to a side of the housing 102 to position the cartridge 120 in an easily accessible position, and to position the cartridge 120 in a substantially vertical orientation. In some embodiments, the cartridge holder 118 is formed by a portion of the housing 102, or is integrally formed with one or more portions of the housing 102. In some embodiments, such as the embodiment illustrated in FIGS. 1-6, the cartridge holder 118 includes a cartridge holder housing 117 positioned to conceal at least a portion of tubing used to fluidly couple one or more of the pump assembly 110, the sample injector 116, the cartridge 120, and the detector 122.

A variety of cartridge holders 118 formed of varying materials and having a variety of shapes can be used to hold the cartridge 120. For example, in some embodiments, the cartridge holder 118 can include a UNIMOUNT™ cartridge bracket, available from Analogix, Inc., Burlington, Wis.

A variety of cartridges 120 can be used with the chromatography system 100. Accordingly, the cartridge holder 118 is adjustable or replaceable to accommodate a wide array of cartridge styles, materials and sizes. In some embodiments, reusable, non-disposable cartridges are used. For example, in some embodiments, the cartridge 120 is formed of glass or metal. In some embodiments, such as the embodiment illustrated in FIGS. 1-6, the cartridge 120 is disposable and formed of a plastic. In some embodiments, the cartridge includes a machine readable identification tag 133, including, but not limited to, a barcode or a radio-frequency identification (RFID) tag. The machine readable identification tag 133 can include information relating to one or more of the following: the size (e.g., length, inner diameter, outer diameter, etc.) of the cartridge 120, mass of the stationary phase 121 inside the cartridge 120, and the type of stationary phase 121 used (e.g., silica, silica-based stationary phases, alumina-based stationary phases, etc., each of which can include irregularly-shaped particles or spherically-shaped particles).

The machine readable identification tag 133 can be added to the exterior of the cartridge 120 (e.g., an adhesive sticker, code written in ink), or the machine readable identification tag 133 can be integrally formed with the cartridge 120 (e.g., written on the outer surface of the cartridge 120 with laser writing). In some embodiments, the chromatography system 100 can be equipped with a reader (e.g., an optical scanner or a RF receiver) to read the machine readable identification tag 133 on the cartridge 120. In some embodiments, reading the machine readable identification tag 133 of a cartridge 120 of interest automatically inputs the necessary data regarding characteristics of the cartridge 120 into the chromatography software, allowing the user to skip having to enter cartridge information during programming or select the cartridge 120 to be used from a list. As a result, the machine readable identification tag 133 can reduce user error and speed up the chromatography programming operation.

Figure 4:
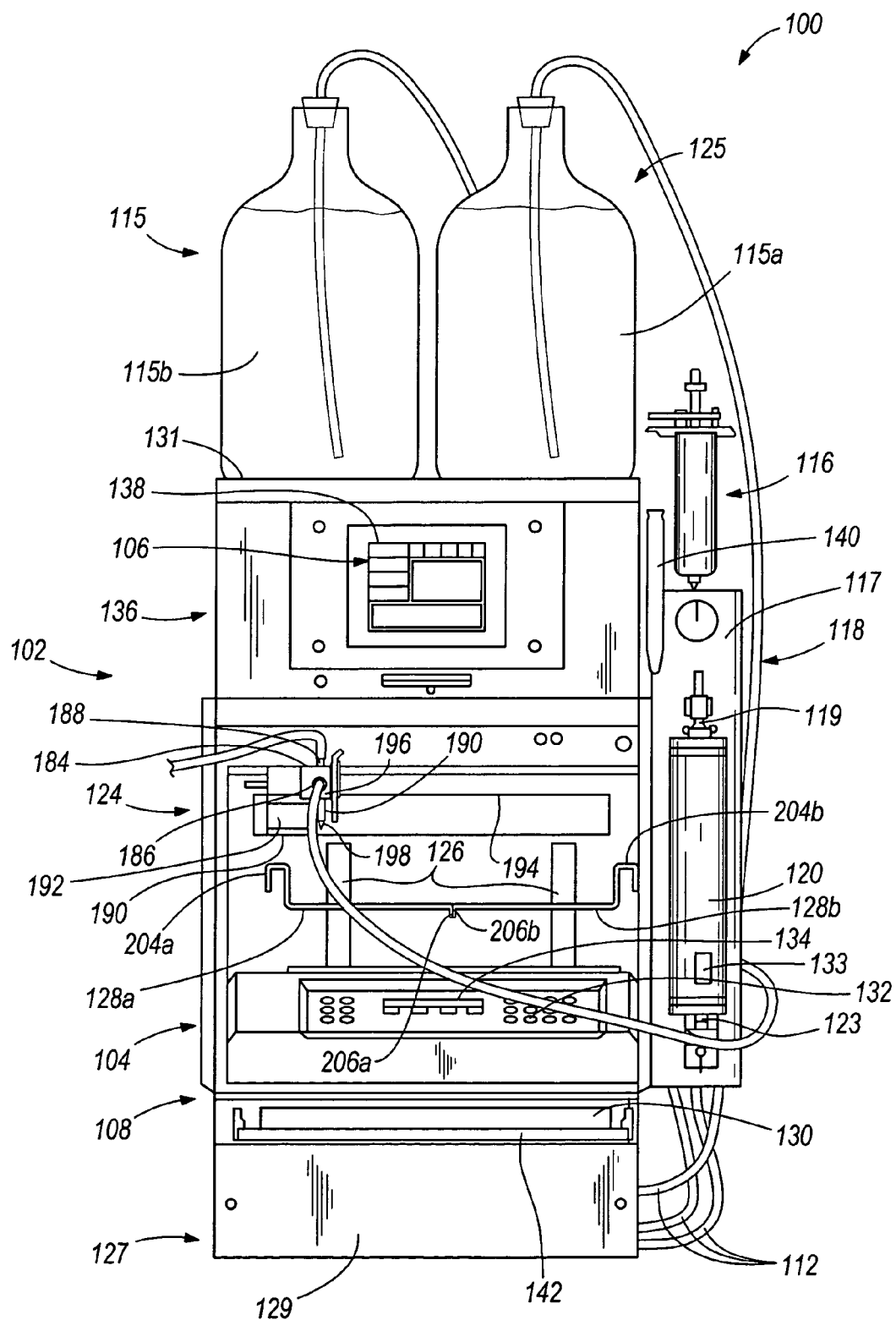
FIG. 4 is a front elevational view of the chromatography system of FIGS. 1-3.

As shown in FIGS. 1 and 4, the machine readable identification tag 133 is positioned on a lower, front portion of the cartridge 120, but it should be understood that the machine readable identification tag 133 can be positioned anywhere on the cartridge 120. In some embodiments, the machine readable identification tag 133 is positioned on the cartridge 120 at a location that will be adjacent or in close proximity to the reader on the chromatography system 100 when the cartridge 120 is positioned for the chromatography process, to allow the machine readable identification tag 133 to be read substantially simultaneously with positioning the cartridge 120 for a chromatography run.

With reference to FIG. 7, the pump assembly 110 is positioned in a forward section of the base portion 127 of the housing 102. The pump assembly 110 includes the pump 114, which moves fluid (e.g., the mobile phase and the sample 101) in the fluid path 112 of the chromatography system 100. The pump 114 is controlled by the controller 104 to pump the fluid in the chromatography system 100 at a given flow rate. In embodiments employing more than one solvent 115, the pump assembly 110 also includes a mixing valve 113 for mixing the solvents 115. The one or more solvents 115 can include, without limitation, at least one of methanol, ethanol, 2-propanol, acetonitrile, ethyl acetate, tetrahydrofuran, acetone, dichloromethane, chloroform, diethyl ether, toluene, hexane, heptane, iso-octane, and combinations thereof. The solvents 115 can be stored and fluidly coupled to the pump assembly 110 in a variety of ways. By way of example only, the embodiment illustrated in FIGS. 1-6 includes containers 125 for storing the solvents 115. The containers 125 are positioned on a tray, or platform, 131 coupled to an upper portion of the monitor 136. Standard tubing and fittings known to those of ordinary skill in the art can be used to fluidly couple the containers 125 to the pump assembly 110.

As shown in FIG. 7, a first solvent 115a enters the base portion 127 of the housing 102 via a first aperture 144a and travels to a first inlet 146a of the mixing valve 113 via tubing 148a. A second solvent 115b enters the base portion 127 of the housing 102 via a second aperture 144b and travels to a second inlet 146b of the mixing valve 113 via tubing 148b.

The mixing valve 113 of the embodiment illustrated in FIG. 7 is a dual gradient mixing valve and includes a first valve 150a and a second valve 150b that control the amount of the first solvent 115a and the second solvent 115b, respectively, in the mobile phase. The valves 150a, 150b shown in the embodiment illustrated in FIG. 7 include magnetically-controlled solenoid valves, but it should be understood that a variety of valves can be used to control the amount of the solvents 115 present in the mobile phase, including, without limitation, a pinch valve, a rotary selector valve, and the like.

The opening of each valve 150a, 150b can be electronically controlled, and therefore can occur substantially instantaneously. The closing of each valve 150a, 150b, however, can be at least partially dependent on the resistance provided by the solvent 115a, 115b, respectively, based on the flow rate, temperature and viscosity of the solvent 115a, 115b. By employing two valves 150a, 150b, when the first valve 150a, for example, is in an open position, the first valve 150a allows the first solvent 115a to enter the mixing valve 113 to be added to the mobile phase of the chromatography system 100. When the mixing valve 113 receives a signal from the controller 104 to add the second solvent 115b to the mobile phase, the second valve 150b will be signaled to move to an open position, and the second solvent 115b will begin being added to the mobile phase. At the same time, the first valve 150a can be signaled to move to a closed position. The closing of the first valve 150a may be at least partially dependent upon the flow rate, temperature and viscosity of the first solvent 115a, but any delay in closing of the first valve 150a will be substantially overridden by the substantially instantaneous opening of the second valve 150b, and any delay that may occur in closing the first valve 150a should not significantly affect the desired concentration of the mobile phase. The illustrated embodiment includes two solvents 115a, 115b, but it should be understood that the mixing valve 113 would function similarly for embodiments employing more than two solvents 115.

After the first solvent 115a and the second solvent 115b have been mixed in the mixing valve 113 to form the mobile phase of the chromatography system 100, the mobile phase exits the mixing valve 113 via an outlet 152 and travels to a connector 154 via tubing 156. The connector 154 shown in FIG. 7 is a Y connector 154 and allows the mobile phase to be directed to a first pump head 158a and a second pump head 158b via a first inlet tube 160a and a second inlet tube 160b, respectively. Each pump head 158a, 158b includes a positive displacement pump. The first pump head 158a and the second pump head 158b are adapted to operate 180 degrees out of phase, such that the first pump head 158a and the second pump head 158b alternate to create a steady flow profile with reduced pulsation and accurate gradient formation in the mobile phase of the chromatography system 100. The first pump head 158a and the second pump head 158b can be easily and quickly replaced, and function together in the pump 114 to produce precise dynamic gradient formation in the mobile phase. In the embodiment illustrated in FIG. 7, the pump 114 includes a binary gradient positive displacement pump, and specifically, an INTELLIFLOW™ low pulsation pump, available from Analogix, Inc., Burlington, Wis. A variety of other pumps or pump heads can be operated in the manner described above to produce a steady flow profile in the mobile phase with reduced pulsation, including, without limitation, a piston pump (e.g., a piston pump available from Fluid Metering, Inc., Syosset, N.Y., or a piston pump available from Diener Precision Pumps), a multiple piston pump (e.g., a SERIES DELTA® multiple piston pump, available from Micropump, Vancouver, Wash.), etc.

Figure 2:
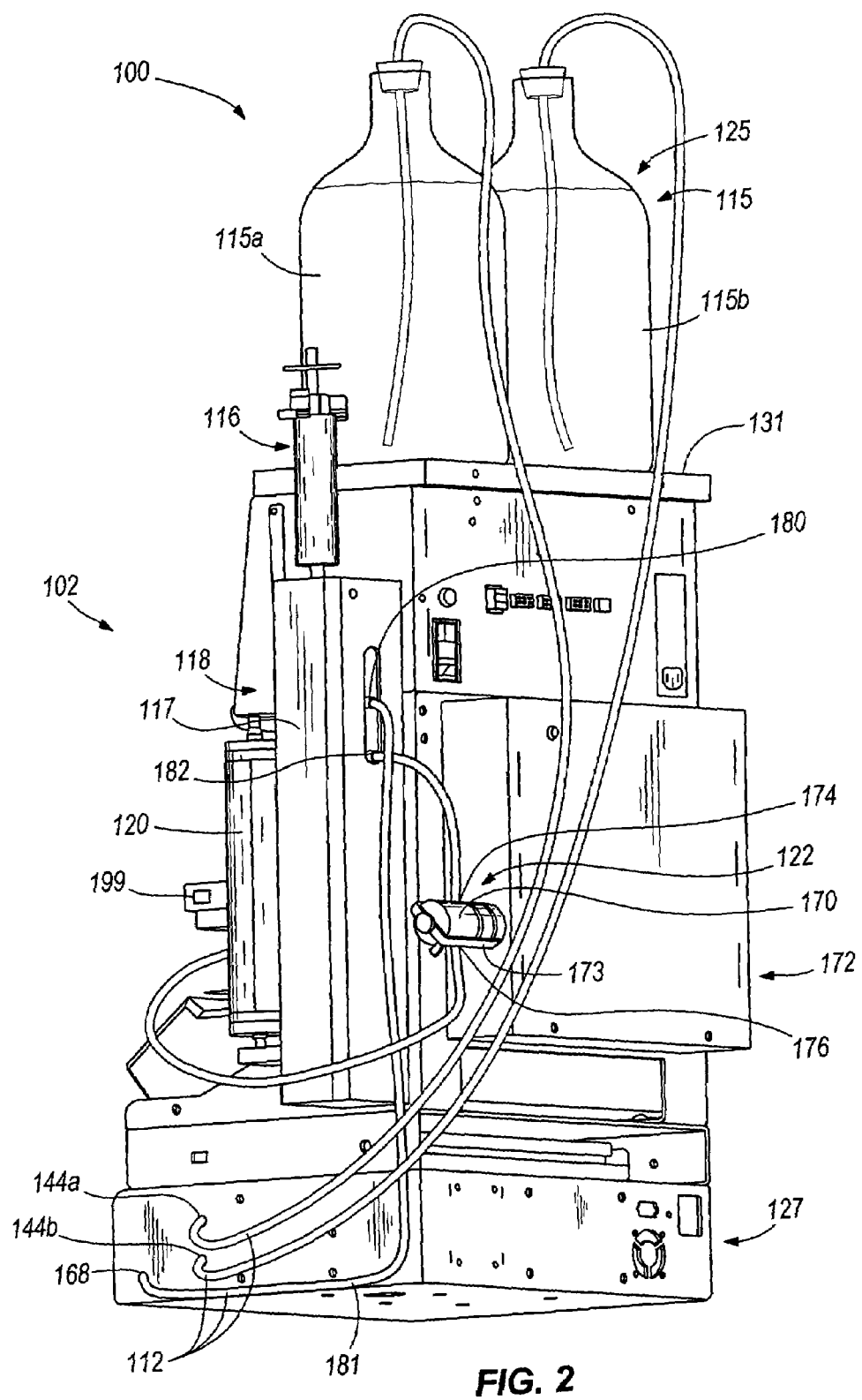
FIG. 2 is a right rear perspective view of the chromatography system of FIG. 1.
Figure 3:
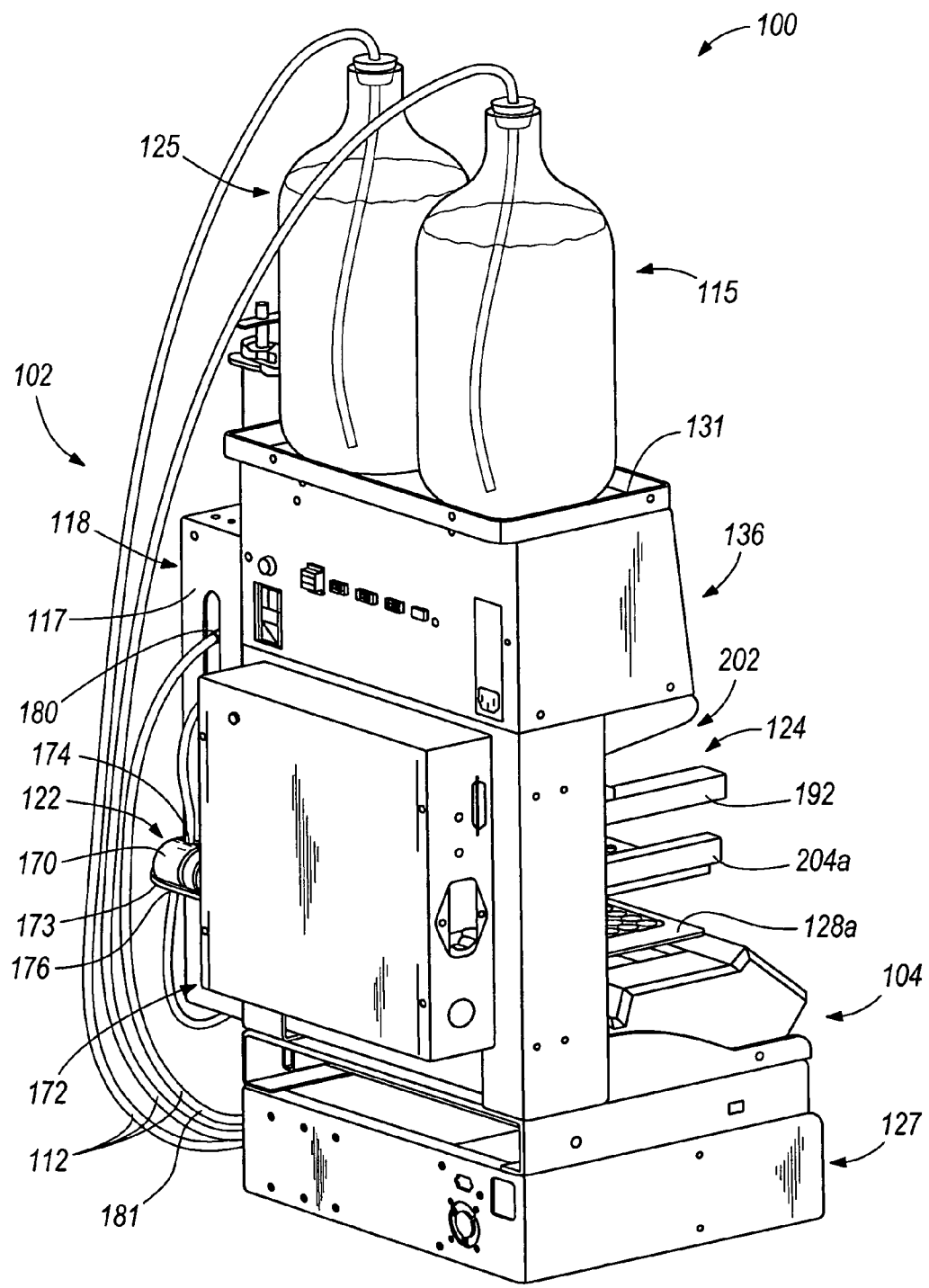
FIG. 3 is a left rear perspective view of the chromatography system of FIGS. 1-2.
Figure 5:
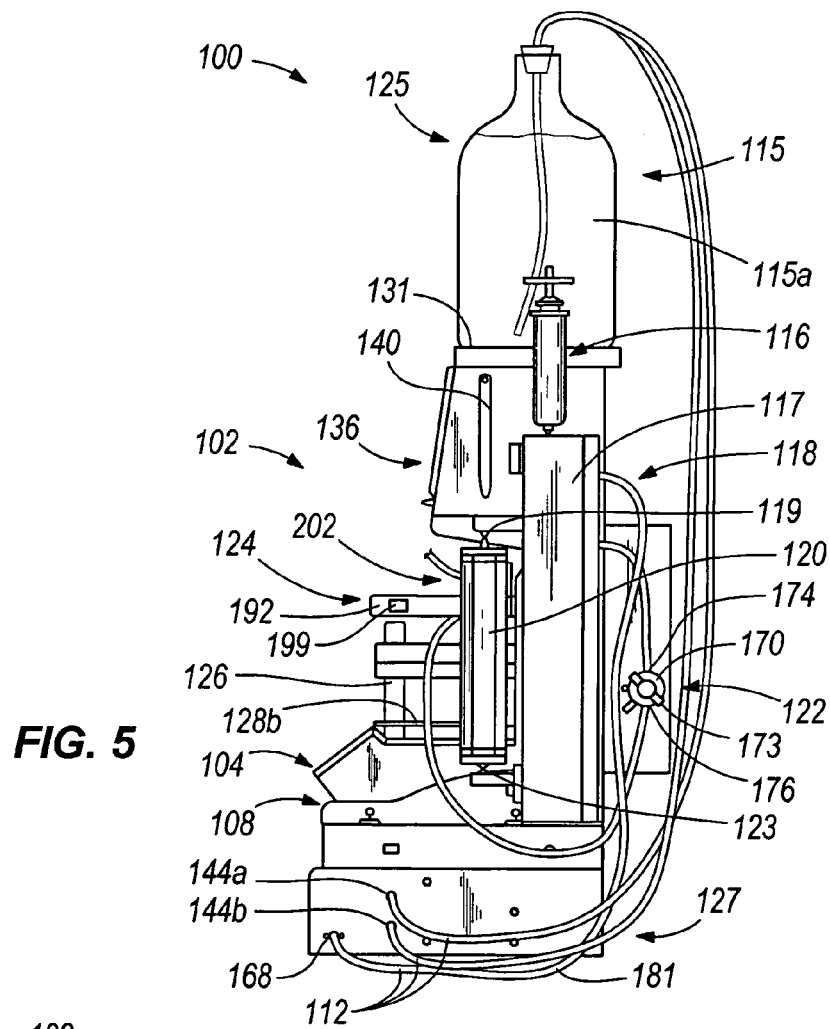
FIG. 5 is a side elevational view of the chromatography system of FIGS. 1-4.
Figure 6:
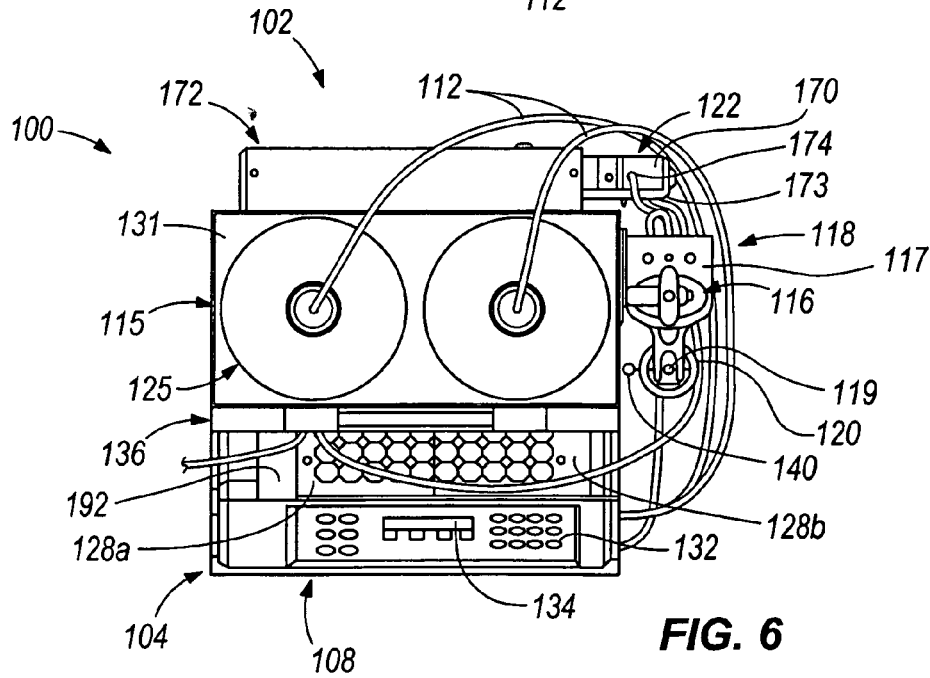
FIG. 6 is a top view of the chromatography system of FIGS. 1-5.

The mobile phase flows out an outlet 162 of the pump 114 to a pressure transducer 164 via outlet tubing 166, before exiting the base portion 127 of the housing 102 via a third aperture 168 in the base portion 127 (see FIGS. 1, 2 and 5). The pressure transducer 164 monitors the pressure in the mobile phase to determine if the fluid pressure produced by the pump 114 is above or below a desired fluid pressure. The pump 114 can then be paused or otherwise adjusted based on feedback received from the pressure transducer 164. For example, the pressure transducer 164 can send information to the controller 104 regarding the fluid pressure. The controller 104 can include a program to automatically pause or otherwise adjust the pump 114 based on the fluid pressure, including, without limitation, when the fluid pressure exceeds a preset threshold or a fixed safety threshold. When the controller 104 pauses the pump 114 in response to the fluid pressure sensed by the pressure transducer 164, the pump 114 can remain paused until a user inactivates the pause. For example, a 'Resume' button can appear in the graphical user interface 106, either in an existing window or in a new window, or a 'Resume' button on the user interface 108 can be pressed.

As shown in FIG. 2, the cartridge holder housing 117 includes a cartridge holder inlet 180 positioned on the back of the cartridge holder housing 117 that is fluidly coupled (e.g., via tubing 181) to the third aperture 168 in the base portion 127 of the housing 102. The cartridge holder inlet 180, in turn, is fluidly coupled to the inlet 119 of the cartridge 120, for example, by tubing positioned within the cartridge holder housing 117. The cartridge holder housing 117 further includes a cartridge holder outlet 182, which is fluidly coupled to the outlet 123 of the cartridge 120, for example, by tubing positioned within the cartridge holder housing 117. The cartridge holder outlet 182 is, in turn, fluidly coupled to the detector 122, as described below. The cartridge holder 118 is shown by way of example only, but it should be understood that the cartridge holder 118 can include a variety of other cartridge mounting means to couple the cartridge 120 to the chromatography system 100. For example, in some embodiments, the cartridge holder 118 does not include a cartridge holder housing 117, and the fluid path 112 is not concealed from the user by any such housing.

As shown in FIGS. 2, 3, 5 and 6, the detector 122 includes a flow cell 170 coupled to a rear portion 172 of the housing 102 with a C-clamp 173. While other means for coupling the flow cell 170 to the chromatography system 100 are possible, the location and coupling means of the flow cell 170 of the illustrated embodiment allow for facile maintenance and replacement. However, other fasteners known to those of ordinary skill in the art can be used in lieu of the C-clamp 173 without departing from the spirit and scope of the present invention.

The rear portion 172 of the housing 102 houses power supply components and components of the controller 104. The detector 122 is positioned downstream of the chromatography cartridge 120 in the fluid path 112. Accordingly, fractions of the sample 101 are moved by the pump 114 from the outlet 123 of the cartridge 120 to an inlet 174 of the flow cell 170. As shown in FIG. 2, in the illustrated embodiment, the fractions of the sample 101 are moved by the pump 114 from the outlet 123 to the cartridge holder outlet 182 to the inlet 174 of the flow cell 170.

At the detector 122, the fluid path 112 is exposed to electromagnetic radiation, and the amount of radiation absorbed by each of the fractions passing through the detector 122 is recorded and used to distinguish the fractions from one another. The fractions of the sample 101 exit the detector 122 via an outlet 176 of the flow cell 170, and continue downstream to the fraction collector 124. The detector 122 includes a transmitter that transmits the radiation to the fluid path 112, and a receiver that receives the radiation that was not absorbed by the fraction of the sample 101 passing through the detector 122 (i.e., transmitted through the sample 101). The receiver sends data to the controller 104 regarding the amount of radiation transmitted through each fraction. The amount of radiation absorbed by each fraction of the sample 101 is calculated, and the absorbance of each fraction is then displayed, usually in graphical form, on the graphical user interface 106. The displayed absorbance data can then be manipulated and analyzed using the chromatography software and graphical user interface 106, as described below.

A variety of detectors 122 can be used to identify and distinguish the fractions, including, without limitation, a UV detector (e.g., an INTELLIUV™ detector, available from Analogix, Inc., Burlington, Wis.), an X-ray detector, an infrared detector, a visible light detector, a refractive index detector (e.g., a refractive index detector available from LabAlliance), a photodiode array (PDA) UV detector, an evaporative light scattering detector (ELSD) (e.g., an ELSD available from Alltech Associates), and the like. In the embodiment illustrated in FIGS. 1-6, the detector 122 includes a fixed UV detector that emits UV radiation having a fixed wavelength. For example, in some embodiments, the detector 122 emits UV radiation having a fixed wavelength of about 254 nm. In some embodiments, the detector 122 includes a variable UV detector that emits a UV radiation having a range of wavelengths. For example, in some embodiments, the detector 122 emits UV radiation having a wavelength ranging from about 200 nm to about 300 nm.

After the fractions of the sample 101 have been detected by the detector 122, peak detecting software identifies and distinguishes the different peaks, and determines a boundary between each "peak" or "non-peak" material in the sample 101. As used herein, the term "fraction" is used to refer to "peak" material, or portions of the sample 101 that a user may wish to detect and/or collect. In some embodiments, the peak detecting software is a peak detecting module within the controller 104. In some embodiments, the peak detecting software communicates with fraction collecting software. The fraction collecting software controls the fraction collector 124, which expels the fractions into one or more collection vessels 126, depending on the algorithm used to distinguish peaks in the peak detecting software, and on user-prescribed settings.

The peak detecting software tells the fraction collecting software whether fluid in the fluid path 112 is "peak" material or "non-peak" material, and whether it should be collected or not. In some embodiments, the peak detecting software functions independently and simply identifies and distinguishes "peak" material from "non-peak" material, and maybe outputs this information to another instrument or other software, but does not control fraction collection. However, in the illustrated embodiment, the peak detecting software communicates with fraction collecting software, and thus, the terms "peak detecting software" and "fraction collecting software" will be used interchangeably herein.

In some embodiments, dual, or multiple, wavelengths can be used in the detector 122 to detect fractions in the sample 101. In some embodiments, dual, or multiple, types of detection (e.g., one UV and one ELSD, etc.) can be used to detect fractions. For example, if two wavelengths (e.g., "colors") of UV detection light are used, two chromatograms will be created and displayed, showing how the fractions of the sample 101 respond to the radiation source in the detector 122. The peak detecting software can then use both chromatograms to distinguish "peak" material from "non-peak" material. A variety of algorithms can be used to accomplish this. For example, in some embodiments, the data points in one chromatogram may be weighted more heavily than data points in another chromatogram. In some embodiments, the peak detecting software may detect a new peak whenever a peak-triggering event occurs in any of the chromatograms. The peak detecting software can then output this information to the fraction collecting software to signal to the fraction collector 124 when to collect a fraction and when to send it to waste. If more than one type of detector 122 is used, the delay volume between detectors 122 would need to be taken into account to synchronize the chromatograms, so that data points relating to the same fraction in the sample 101 can be correlated. The delay volume between subsequent detectors can be entered into or calculated given the size (e.g., length and cross-sectional diameter or area) of tubing connecting an outlet of a first detector 122 and an inlet of a second detector 122, and so on.

As best shown in FIG. 1, the fraction collector 124 includes an arm 192 movable along a track 194 in an x-direction, the arm 192 having a length in a y-direction, substantially perpendicular to the x-direction. The fraction collector 124 further includes a carriage 196 coupled to the arm 192 and movable along the length of the arm 192 in the y-direction. The carriage 196 includes a downwardly-directed nozzle 198 from which the one or more fractions of the sample 101 can be expelled into one or more collection vessels 126. The arm 192 and carriage 196 allow the nozzle 198 to be positioned in an x-y plane above the collection vessels 126. The carriage 196 can further include z-positioning means for moving the nozzle 198 in a z-direction, orthogonal to the x-y plane, toward and away from the collection vessels 126. Other types of carriages or gantry systems having movement in one ore more of the x-direction, the y-direction and the z-direction can be used to position the nozzle 198 over a desired collection vessel 126 for expulsion of one or more fractions of the sample 101, without departing from the spirit and scope of the present invention.

As shown in FIGS. 1 and 4, the fraction collector 124 includes a divert valve 184 that includes an inlet 186 that is fluidly coupled to the outlet 176 of the flow cell 170 of the detector 122. Depending on the collection mode of the fraction collecting software, which will be described below, the fraction collecting software determines whether the fraction of the sample 101 is sent to a first outlet 188 of the divert valve 184, which is fluidly coupled to waste, or a second outlet 190 of the divert valve 184, which is fluidly coupled to the nozzle 198. As a result, fractions that are not to be collected will be directed to the first outlet 188 of the divert valve 184 to waste, and fractions that are to be collected will be directed to the second outlet 190 of the divert valve 184 and dispensed out of the nozzle 198 of the fraction collector 124 and into a collection vessel 126.

In some embodiments, a user may wish to perform thin layer chromatography (TLC) with the contents of a collection vessel 126 by extracting a sample from a collection vessel 126 of interest and spotting the sample onto a TLC plate. In some embodiments, this is performed manually. In some embodiments, the fraction collector 124 can be programmed to automatically spot a TLC plate with each new fraction from the sample 101 that is about to be added to a new collection vessel 126 (or at the very end of a collection). Alternatively, the user can instruct the fraction collector 124, when desired, to spot a TLC plate with a desired fraction. In such embodiments, the carriage 196 of the fraction collector 124 can include mobility in the X-Y plane independent of the arm 192 to move away from the arm 192 to a TLC plate. In addition, the carriage 196 can include mobility in the z-direction to move toward and away from a TLC plate.

In some embodiments, the user can select to perform TLC with at least a portion of the contents of each collection vessel 126 after a chromatography run has completed. In some embodiments, the user can select to perform TLC with at least a portion of one collection vessel 126 corresponding to each detected fraction (i.e., some fractions can require more than one collection vessel 126), such as the first collection vessel 126 of a particular fraction, a middle collection vessel 126 of a particular fraction, the last collection vessel 126 of a particular fraction, the first and last collection vessels 126 of a particular fraction, etc. In some embodiments, the user can select to perform TLC with at least a portion of the collection vessel 126 corresponding to a fraction having the highest detected concentration (i.e., highest absorbance units measured by the detector 122). In some embodiments, the user can select to perform TLC with at least a portion of the collection vessel 126 corresponding to a fraction having the highest or lowest slope of absorbance detected by the detector 122 (i.e., the greatest increase or decrease in detected concentration).

As mentioned above, the fractions of the sample 101 can be collected in one or more collection vessels 126 positioned in one or more collection vessel stands 128. In some embodiments, as shown in FIGS. 1, 2 and 5, the collection vessel stand(s) 128 includes a machine readable identification tag 199, including, but not limited to, a barcode, a radio-frequency identification (RFID) tag, a magnetically activated identification tag (e.g., as available from Omron Corporation), an electrically conductive identification tag (e.g., an IBUTTON® series electrically conductive identification tag, available from Dallas Semiconductor), etc. The machine readable identification tag 199 can include a variety of information, including, but not limited to: the size of the collection vessel stand 128; the size of collection vessels 126 stored in the collection vessel stand 128; the number of collection vessels 126 the collection vessel stand 128 can hold; data relating to the contents of the collection vessels 126 in the collection vessel stand 128; data identification such that a chromatogram relating to the contents of the collection vessel stand 128 can be accessed by reading the machine readable identification tag 199; and a globally unique identifier (GUID) to definitively identify the collection vessel stand 128 from all others. A GUID allows the chromatography system 100 and any other instrument that may use or analyze the fractions of the sample 101 to be able refer to a common database, so that one instrument can add information to the collection vessel stand 128 identified via the GUID, and another can access the information, and vice versa.

The machine readable identification tag 199 can be added to the collection vessel stand 128 (e.g., an adhesive sticker, code written in ink, a physical tag coupled to the collection vessel stand 128 by a variety of fasteners, including, without limitation, one or more of a screw, nail, bolt, snap-fitting, press-fitting, and the like), or the machine readable identification tag 199 can be integrally formed with the collection vessel stand 128 (e.g., written on the outer surface of the cartridge 120 with laser writing). In some embodiments, the chromatography system 100 can be equipped with a reader (e.g., an optical scanner, a RF receiver, a magnetic reader, an electrical conduction reader, etc.) to read the machine readable identification tag 199. In some embodiments, the machine readable identification tag 199 can be read manually by a user, and the appropriate number or other identifier can be entered (e.g., by typing, speaking, or selecting from a list).

The position of the machine readable identification tag 199 is shown in FIGS. 1, 2 and 5 by way of example only, but it should be understood that the machine readable identification tag 199 can be positioned anywhere on the collection vessel stand 128. In some embodiments, the machine readable identification tag 199 is positioned on the collection vessel stand 128 at a location that will be adjacent or in close proximity to the reader on the chromatography system 100 when the collection vessel stand 128 is positioned in the recess 202 of the housing 102, to allow the machine readable identification tag 199 to be read substantially simultaneously with positioning the collection vessel stand 128 for a chromatography run.

In some embodiments, reading or entering the machine readable identification tag 199 of a collection vessel stand 128 of interest automatically inputs the necessary data regarding characteristics of the collection vessel stand 128 into the chromatography software, allowing the user to skip having to enter collection vessel stand 128 information during programming or select the collection vessel stand 128 to be used from a list. As a result, the machine readable identification tag 199 can reduce user error and speed up the chromatography programming operation. Furthermore, because the chromatography programming software will have information about the collection vessel stand 128 being used, the controller 104 can pause the pump 114 when the collection vessel stand 128 no longer includes an empty collection vessel 126 available for the fraction collector 124. When the controller 104 pauses the pump 114, the pump 114 can remain paused until a user inactivates the pause. For example, a 'Resume' button can appear in the graphical user interface 106, either in an existing window or in a new window, or a 'Resume' button on the user interface 108 can be pressed.

In some embodiments, the collection vessel stand 128 is reusable and non-disposable, and is formed of a material such as metal. In some embodiments, the collection vessel stand 128 is disposable and formed of a material such as plastic. In some embodiments, the collection vessel stand 128 is pre-filled with collection vessels 126 to eliminate the time-consuming process of filling the collection vessel stand 128. For example, in some embodiments, the collection vessel stand 128 can include a plurality of integrally-formed collection vessels 126 (e.g., a molded tray, a thermoformed tray, etc.) to eliminate having to fill the collection vessel stand 128 with collection vessels 126, or have the collection vessel stand 128 pre-filled with collection vessels 126. In some embodiments, a plurality of collection vessels 126 can be integrally formed and have dimensions compatible with the collection vessel stand 128 to allow a plurality of collection vessels 126 to be loaded into a collection vessel stand 128 at once. For example, a strip of collection vessels 126 having a length compatible with a length of the collection vessel stand 128 can be used to fill one row in collection vessel stand 128 at a time.

In some embodiments, as shown in FIGS. 1-6, the type of collection vessel 126 used is a test tube 126, and accordingly, the type of collection vessel stand 128 used is a test tube rack 128. In the embodiment illustrated in FIGS. 1-6, the housing 102 includes a recess 202 defined between an upper portion of the controller 104 and a lower portion of the monitor 136. The recess 202 defines a collection vessel stand holder 135 and is dimensioned to receive one or more collection vessel stands 128, shown in FIGS. 1-6 as test tube racks 128.

In some embodiments, the chromatography system 100 includes one test tube rack 128, which can be positioned in the recess 202. After the fractions of the sample 101 have been expelled into one or more test tubes 126 in the test tube rack 128, the test tube rack 128 can be removed and replaced with a new test tube rack 128 that includes empty test tubes 126 ready to be filled by additional fractions from the sample 101, or fractions from a new sample. However, the chromatography process may have to be paused to allow for removal and/or replacement of the test tube rack 128.

In the embodiment illustrated in FIGS. 1-6, the chromatography system 100 includes two test tube racks 128a, 128b that are positioned on top of the controller 104 in the recess 202. The two test tube racks 128a, 128b are identical and essentially have the appearance of one split test tube rack 128. For simplicity, the split test tube rack 128 will be described as two test tube racks 128a, 128b herein. Each test tube rack 128a, 128b includes a handle 204a, 204b to allow a user to grasp the test tube rack 128a, 128b during placement or removal of the test tube rack 128a, 128b from the recess 202. Each of the two test tube racks 128a, 128b includes a flat edge 206a, 206b. Each flat edge 206a, 206b can be placed in abutting relationship with the other flat edge 206b, 206a of the adjacent test tube rack 128b, 128a, respectively. Employing two test tube racks 128a, 128b allows a user to remove or replace one test tube rack 128a, 128b while the other test tube rack 128b, 128a, respectively, is being filled by the fraction collector 124. The process of replacing the test tube rack 128a, 128b that is currently not in use can be repeated indefinitely without interrupting the chromatography process to collect a large number of fractions. The LCD screen 134 on the touchpad 132 can display information relating to whether the test tube racks 128a, 128b are full or empty, and when they can be replaced. Alternatively, this information can be displayed on the monitor 136.

FIGS. 8-20 illustrate a variety of screen shots of the graphical user interface 106 of the chromatography software of the chromatography system 100, which will now be described in detail. The chromatography software can include a variety of software, including, for example, the INTELLIPEAK™ chromatography programming software described above. As shown in FIGS. 8-20, the graphical user interface 106 of the chromatography software includes a wizard program 220 that guides a user through the process of creating a chromatography run for the sample 101 of interest. The wizard program 220 includes a main window 221 that includes four screens: a 'General' screen 222 (see FIG. 8), a 'Detection' screen 224 (see FIG. 14), a 'Pump' screen 226 (see FIG. 16), and a 'Chromatogram' screen 228 (see FIG. 17). The four screens 222, 224, 226, 228 are separated in a tabular format in the main window 221, and each screen 222, 224, 226, 228 can be accessed by selecting the corresponding tab at the top of the main window 221. It should be noted that the wizard program 220 can include as few as one screen and as many as desired to accomplish a variety of tasks, such as those described in greater detail below.

The main window 221 includes a static region 227 to allow a portion of the window 221 to be visible on each screen 222, 224, 226, 228. The static region 227 can include one or more of the following: a 'Sample ID' field 229 to record (e.g., using the keyboard 130) a name or number to identify the sample 101; a method file title field 231 to display the method being used and/or created; a 'Run' button 230, which can be selected to begin a chromatography run in the chromatography system 100; and a lamp button 233 (e.g., identified by a light bulb icon, as shown in the illustrated embodiment), which illustrates when the radiation source (e.g., a UV lamp) is powered on in the detector 122.

Figure 8:
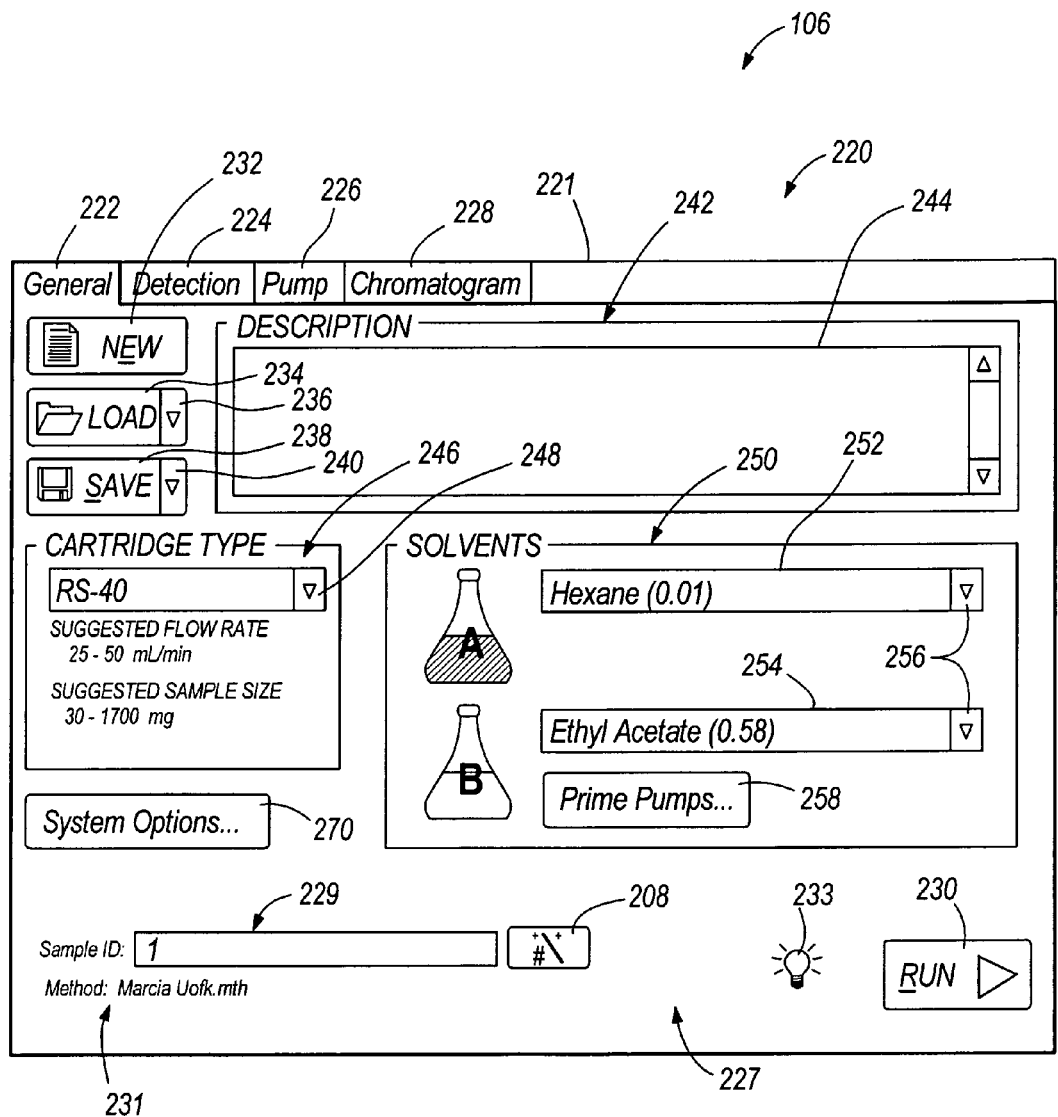
FIGS. 8-20 illustrate various screen shots of a graphical user interface according to one embodiment of the present invention.
Figure 8B:
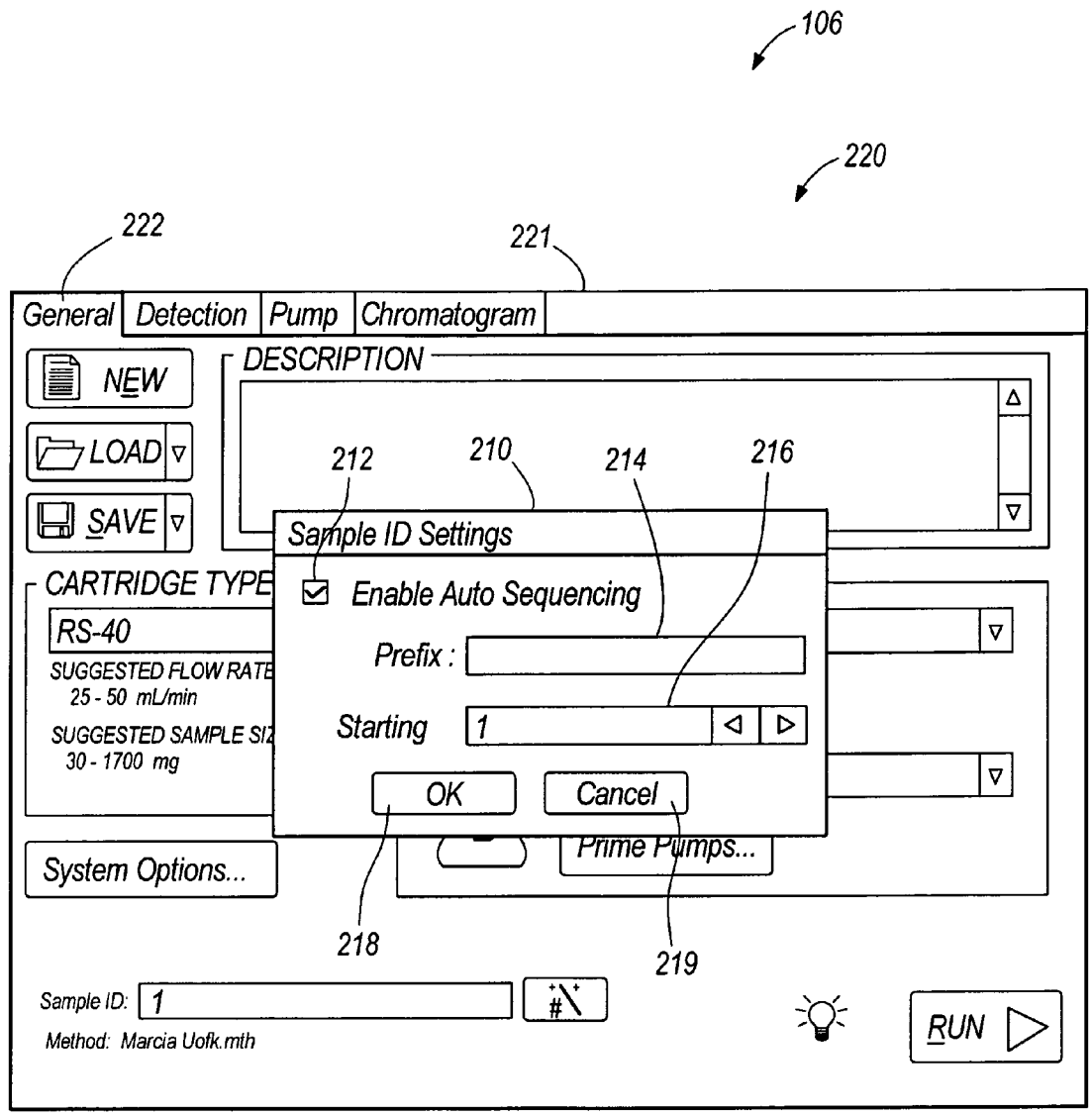

The 'Sample ID' field 229 includes a sample identity wizard button 208. Selecting the sample identity wizard button 208 opens a 'Sample ID Settings' window 210, as shown in FIG. 8B. The 'Sample ID Settings' window 210 includes an 'Enable Auto Sequencing' checkbox 212, a 'Prefix' field 214, a 'Starting' field 216, an 'OK' button 218 which can be selected when the user is satisfied with the sample identity settings, and a 'Cancel' button 219 if the user does not wish to change or enter any data in the 'Sample ID Settings' window 210. When the 'OK' button 218 is selected, the user will be returned to the 'General' screen 222. FIG. 8B illustrates one embodiment of auto sequencing sample identities. In the embodiment illustrated in FIG. 8B, the auto-sequencing feature includes a fixed portion of a sample ID and a variable or auto-incrementing portion of the sample ID. The user can enter a fixed portion of a sample identity in the 'Prefix' field 214, and can use the 'Starting' field 216 to specify a number from which to begin counting or incrementing to create a sequence of related runs.

After powering up, the chromatography software generally defaults to the 'General' screen 222 of the wizard program 220. FIG. 8 illustrates the 'General' screen 222 according to one embodiment of the invention. As shown in FIG. 8, the 'General' screen 222 includes a 'New' button 232. Selecting the 'New' button 232 creates a new method file and clears all data to reset the functions of the chromatography system 100. In some embodiments, after selecting the 'New' button 232, a dialog box will appear to ask the user, "Do you want to clear you current method settings?" and will include a 'No' button and a 'Yes' button. Selecting the 'Yes' button will require the user to either enter a new method or load an existing method file.

The 'General' screen 222 further includes a 'Load' button 234, which can be selected to find and select a saved method file (e.g., a *.mth file) from a Windows CE™-based browsing window. The 'Load' button 234 includes a load drop-down menu button 236. Selecting the load drop-down menu button 236 activates a list of a variety of loading menu options, including, without limitation, at least one of 'Load Method,' which, if selected, loads an existing method from memory within the controller 104, a removable memory storage device (e.g., a Compact Flash card, a floppy disk, a compact disk (CD), etc.) or another computer that is connected to the controller 104 via a hard-wired or wireless connection; 'Load Last Run,' which, if selected, loads the last method run on the chromatography system 100; and 'Load Results File,' which, if selected, displays a list of automatically saved results files (e.g., a *.alx file).

The 'General' screen 222 further includes a 'Save' button 238, which can be selected to archive method data to memory (e.g., as a *.mth file) using a Windows CE™-based browsing window. The 'Save' button 238 includes a save drop-down menu button 240. Selecting the save drop-down menu button 240 activates a list of a variety of saving menu options, including, without limitation, at least one of 'Save Method,' which, if selected, performs the same command as selecting the Save button 238; and 'Save Results,' which, if selected, opens a browser window to, allowing a user to save the current chromatography run as a result. In some embodiments, the chromatography software automatically saves chromatography runs that last greater than three minutes when the run is completed.

The 'General' screen 222 further includes a 'Description' field 242, which includes a text field 244. A user can annotate the chromatography run by adding text to the text field 244. In some embodiments, the text in the text field 244 will automatically be saved with the method when the method is saved.

The 'General' screen 222 further includes a 'Cartridge Type' field 246, which allows a user to choose the type of chromatography cartridge 120 to be used in the chromatography run. The chromatography cartridge 120 can be chosen based on the size/amount of the sample 101 of interest and a retention factor ($R_F$) value. The 'Cartridge Type' field 246 includes a cartridge drop-down menu button 248, which, when selected, provides a list of a variety of cartridges 120 available to the user. By selecting a 'System Options . . . ' button 270, described below, the user can navigate to the location of a cartridge configurable text file to allow the user to build and modify the drop-down menu list for his/her needs. The cartridges 120 can be listed by product name, product no., model name, model no., size of the cartridge 120 (e.g., length, inner diameter, outer diameter, etc.), mass of the stationary phase 121 in the cartridge 120, and combinations thereof.

The configurable text file can be in a table format, and can include a variety of fields, including, without limitation, at least on of ID no., cartridge volume (CV), equilibration time (e.g., in seconds), equilibration flow volume (e.g., in mL), purify flow volume (e.g., in mL), minimum flow volume (e.g., in mL), maximum flow volume (e.g., in mL), minimum sample size (e.g., in mg), maximum sample size (e.g., in mg), purge time (e.g., in seconds), maximum pressure able to withstand (e.g., in psi), inside diameter, outside diameter, length, suggested flow rate (or minimum and maximum suggested flow rates), cross-sectional area, display description (i.e., how the cartridge will be identified in the drop-down menu), comments, product family name, product name, etc. Other computations can be performed using data from one or more of these fields. For example, in some embodiments, as shown in FIG. 8, after a cartridge 120 is selected from the list (e.g., RS-40, as shown in FIG. 8), a suggested flow rate and sample size for the cartridge 120 selected will appear in the 'Cartridge Type' field 246 (e.g., 25-50 mL/min. and 30-1700 mg, as shown in FIG. 8), based on the data listed in the corresponding fields for the cartridge selected.

The 'General' screen 222 further includes a 'Solvents' field 250, which allows selection and identification of the solvents 115 to be used. The 'Solvents' field 250 includes a first solvent field 252, named 'A' in FIG. 8, and a second solvent field 254, named 'B' in FIG. 8. Each of the first and second solvent fields 252, 254 includes a solvent drop-down menu button 256, which, when selected, provides a list of available solvents that a user can select. In embodiments employing more than two solvents 115, the Solvents field 250 includes a solvent field for every solvent 115 to be used. In some embodiments, the user can choose a solvent from the list, or the user can enter a new solvent name in at least one of the first solvent field 252 and the second solvent field 254 using the keyboard 130. In some embodiments, a newly entered solvent name can be stored when the method is saved. In some embodiments, a newly entered solvent name can be saved when a run is initiated for longer than a predetermined amount of time (e.g., 3 minutes). The 'Solvents' field 250 further includes a 'Prime Pumps . . . ' button 258. The 'Prime Pumps . . . ' button 258, when selected, opens a 'Prime Pumps' window 260, as shown in FIG. 9.

Figure 9:
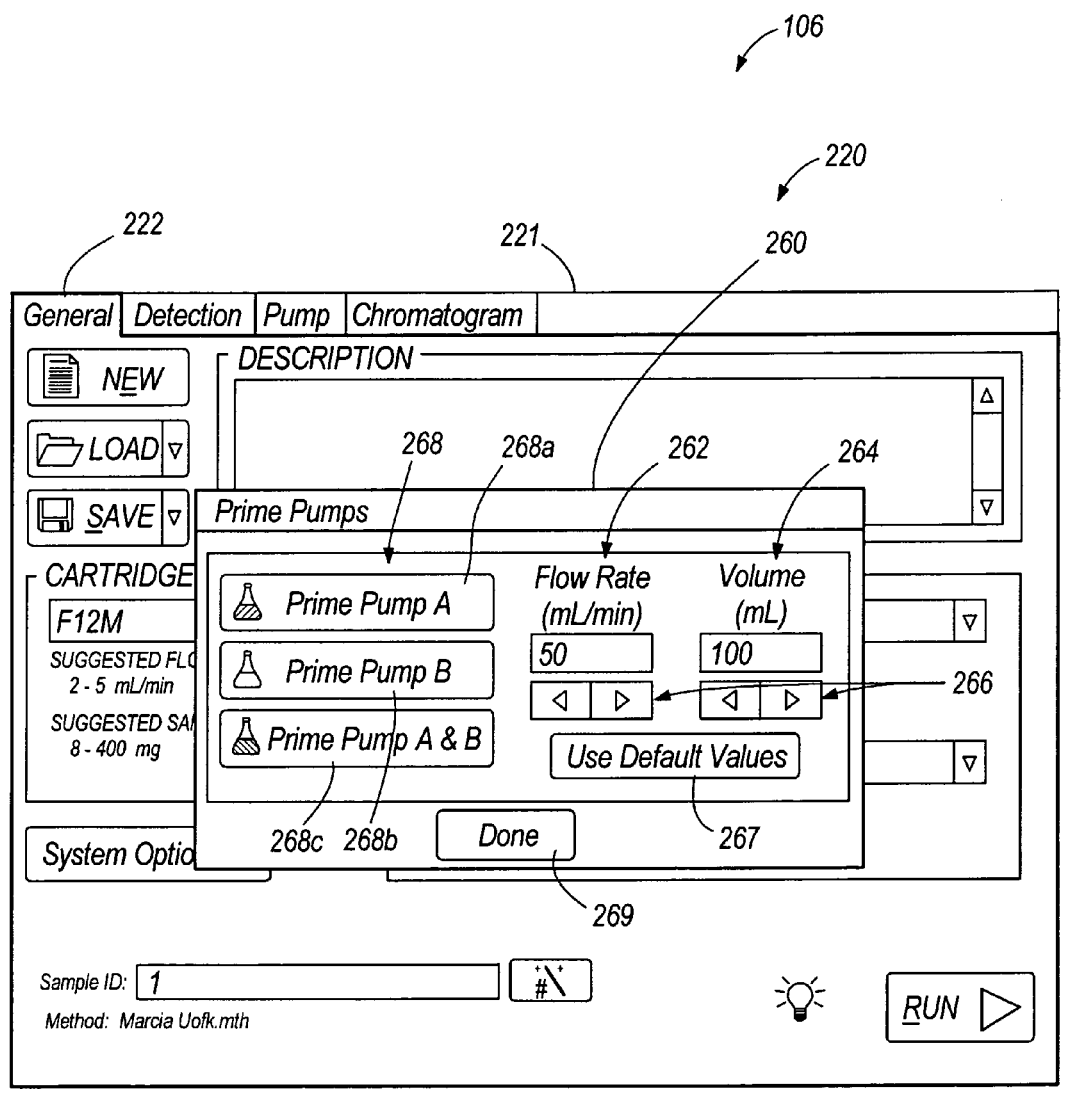

With reference to FIG. 9, the 'Prime Pumps' window 260 includes a 'Flow Rate' field 262 and a 'Volume' field 264 with incrementing buttons 266. A user can set a flow rate and volume for each solvent 115 to be used by using the keyboard 130 to type in the 'Flow Rate' field 262 and the 'Volume' field 264, or by using the incrementing buttons 266 to increase or decrease the values displayed. A user can instead select a 'Use Default Values' button 267 to select system default settings, which can be stored in a configurable text file. The configurable text file can be accessed by selecting the 'System Options . . . ' button 270. Alternatively, in some embodiments (not shown), one of the screens 222, 224, 226, 228 (e.g., the 'General' screen 222) can include a button that directs the user to a 'Cartridge Editor' screen, which will allow the user to edit the configurable text file using some type of word-processing program (e.g., MICROSOFT® Windows NOTEPAD™ word processing application). A user can also select one or more priming buttons 268 to prime the first pump head 158a (i.e., by selecting the 'Prime Pump A' button 268a), the second pump head 158b (i.e., by selecting the 'Prime Pump B' button 268b), or both (i.e., by selecting the 'Prime Pumps A & B' button 268c). When the flow rates and volumes for the solvents 115 have been set, and the desired pump heads 158a, 158b primed, the user can select a 'Done' button 269 to return to the 'General' screen 222.

With continued reference to FIG. 8, the 'General' screen 222 further includes the 'System Options . . . ' button 270. When the 'System Options . . . ' button 270 is selected, a 'System Options' window 272 is opened, as shown in FIGS. 10-13B. The 'System Options' window 272 allows a user to select a variety of settings and defaults in the chromatography system. With reference to FIGS. 10-13B, the 'Systems Options' window 272 includes five screens that are separated in a tabular format: a 'System' screen 274, a 'Solvents' screen 276, a 'System Info' screen 278, a 'Control Panel' screen 280, and a 'Calibration' screen 281. Each screen 274, 276, 278, 280, 281 includes a 'Save & Close' button 282. Selecting the 'Save & Close' button 282 will save the selections chosen and return to the 'General' screen 222.

Figure 10:
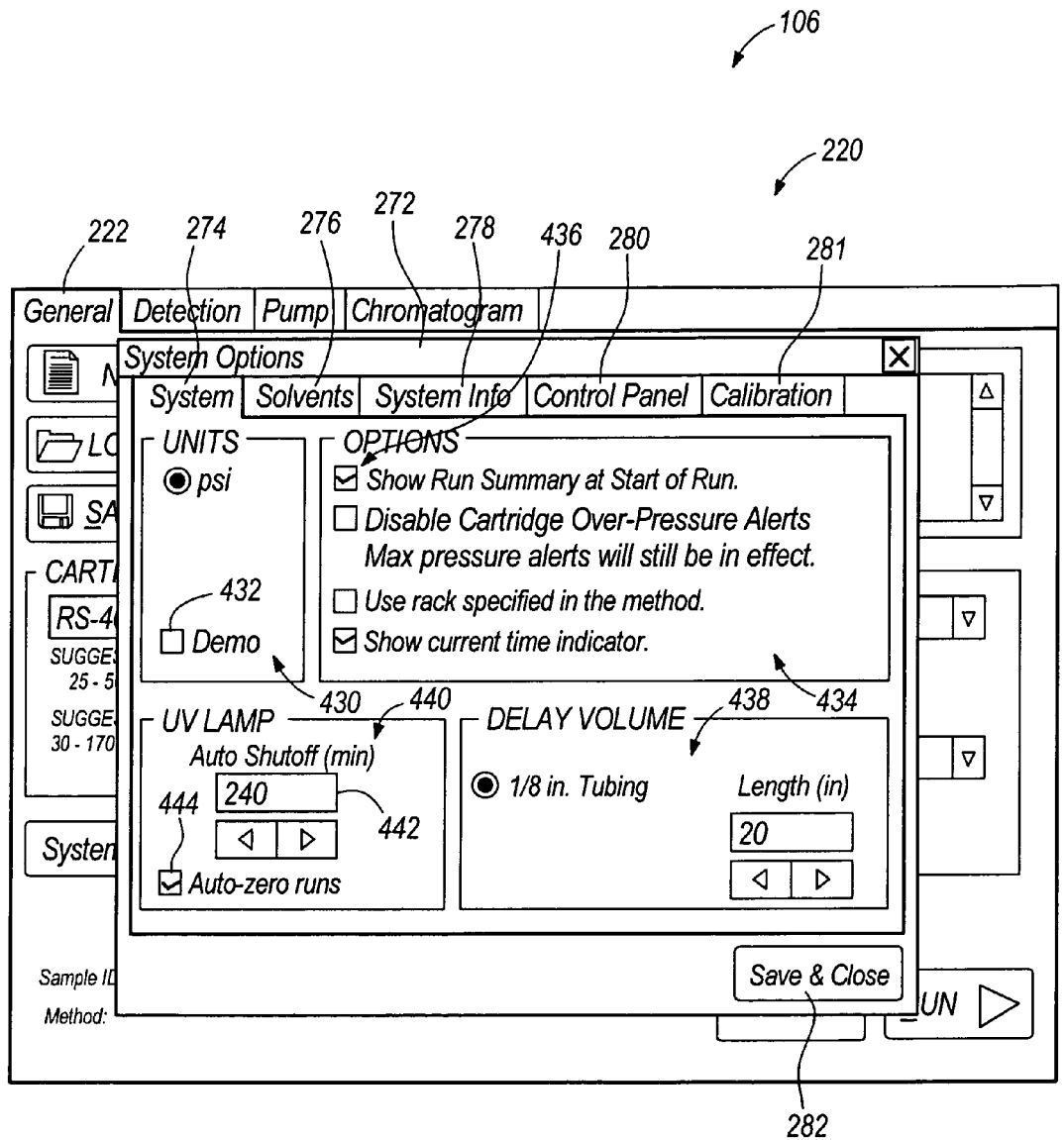

As shown in FIG. 10, the 'System' screen 274 includes a 'Units' field 430, which allows the selection of pressure units in the system (e.g., psi, as shown in FIG. 10), and includes a 'Demo' checkbox 432. Checking the 'Demo' checkbox 432 creates a chromatogram based on data points stored in a file, and does not actually run the pump assembly 110 or the detector 122, but will operate the fraction collector 124, and allows a user to demonstrate how the chromatography system 100 works, without actually running a sample 101.

The 'System' screen 274 further includes an 'Options' field 434, where a variety of checkboxes 436 can be selected or deselected depending on user preferences. For example, the user can select a 'Use rack specified in the Method' checkbox to store which collection vessel stand 128 the user wishes to use with the method file (*.mth) created, so that each time that method file is loaded, the collection vessel stand 128 settings are already in place. In addition, a 'Show current time indicator' checkbox allows a user to select whether a vertical line will be shown in a chromatogram that clearly shows the point in time corresponding with each data point in the chromatogram.

The 'System' screen 274 further includes a 'Delay Volume' field 438, which allows for selection of a tubing size (e.g., cross-sectional diameter or area) and a length between the outlet 176 of the flow cell 170 of the detector 122 and the inlet 186 of the divert valve 184 of the fraction collector 124. The cross-sectional area and length of tubing positioned between the inlet 176 and the outlet 186 can allow for calculation of a delay volume, which is explained in greater detail below.

The 'System' screen 274 can further include a 'UV Lamp' field 440, which includes an 'Auto Shutoff (min)' text field 442, which allows a user to enter or select an amount of time the detector lamp (UV or otherwise) will remain powered on before it automatically is powered off by the controller 104. The 'UV Lamp' field 440 further includes an 'Auto-zero runs' checkbox 444, which can be selected to signify that the detector should be zeroed before each chromatography run.

Figure 11:
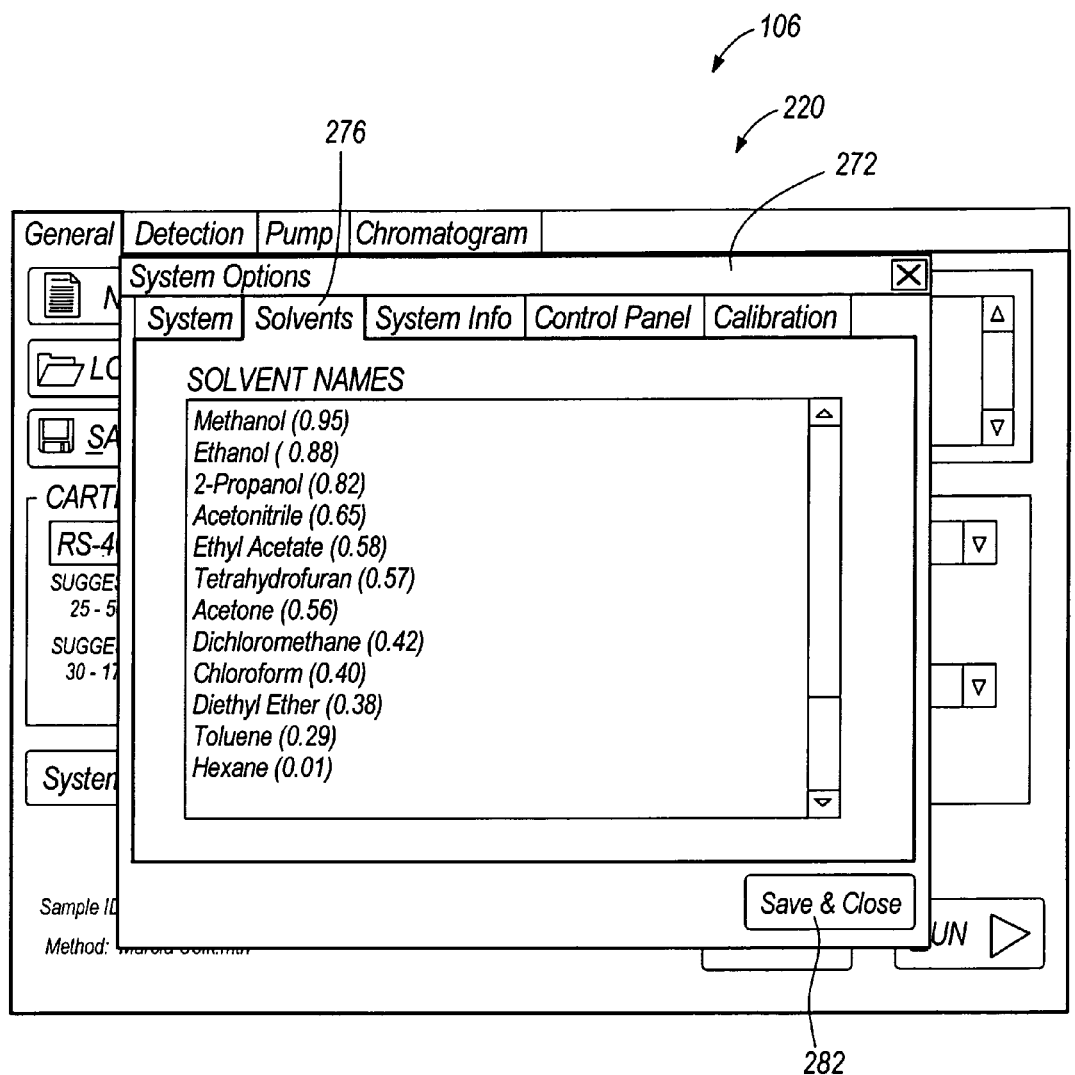

As shown in FIG. 11, the 'Solvents' screen 276 includes a list of solvent names (and their relative strengths (e.g., polarity) shown in parentheses after the solvent name). Selecting the 'Solvents' screen 276 in the 'System Options' window 272 provides access to this list of solvents, which may be edited in the 'Solvents' screen 276, or which may be edited in a configurable text file that the 'Solvents' screen 276 accesses. Editing the list of solvent names changes what is displayed in the drop-down menus 256 in the 'General' screen 222. The list of solvent names and/or the configurable text file can be in a table format, and in addition to a list of solvent names, can also include solvent properties, including, without limitation, at least one of density, boiling point, melting point, molecular weight, water solubility, chemical formula, vapor pressure, vapor density, etc.

Figure 12:
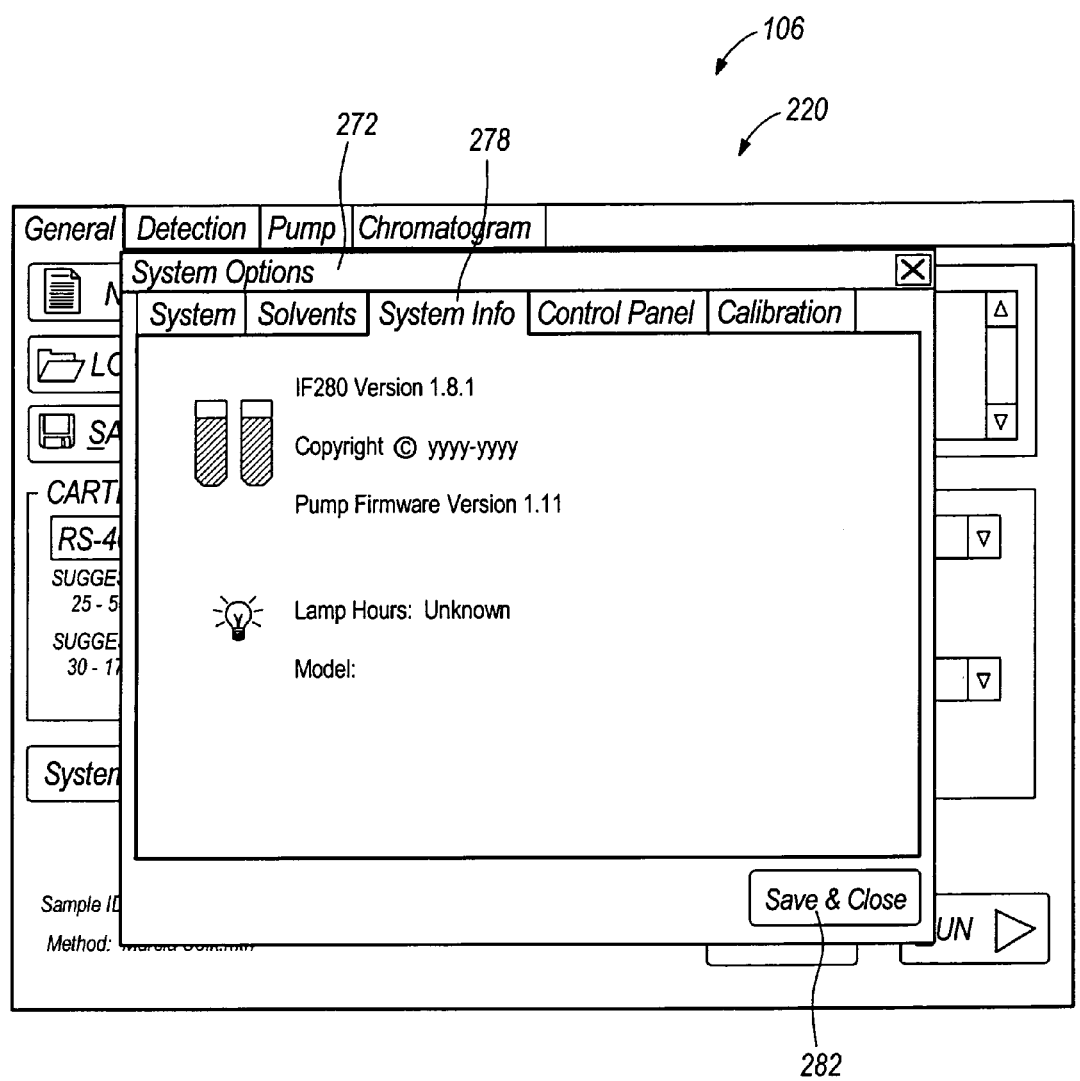

As shown in FIG. 12, the 'System Info' screen 278 displays a variety of information about the chromatography system 100, including the version of the chromatography system 100 and/or software being used, copyright information, which version of firmware for the pump 114 is being used, and the remaining hours of operation for the radiation source in the detector 122. It should be understood that the 'System Info' screen 278 can be used to display a variety of other parameters of the chromatography system 100.

Figure 13:
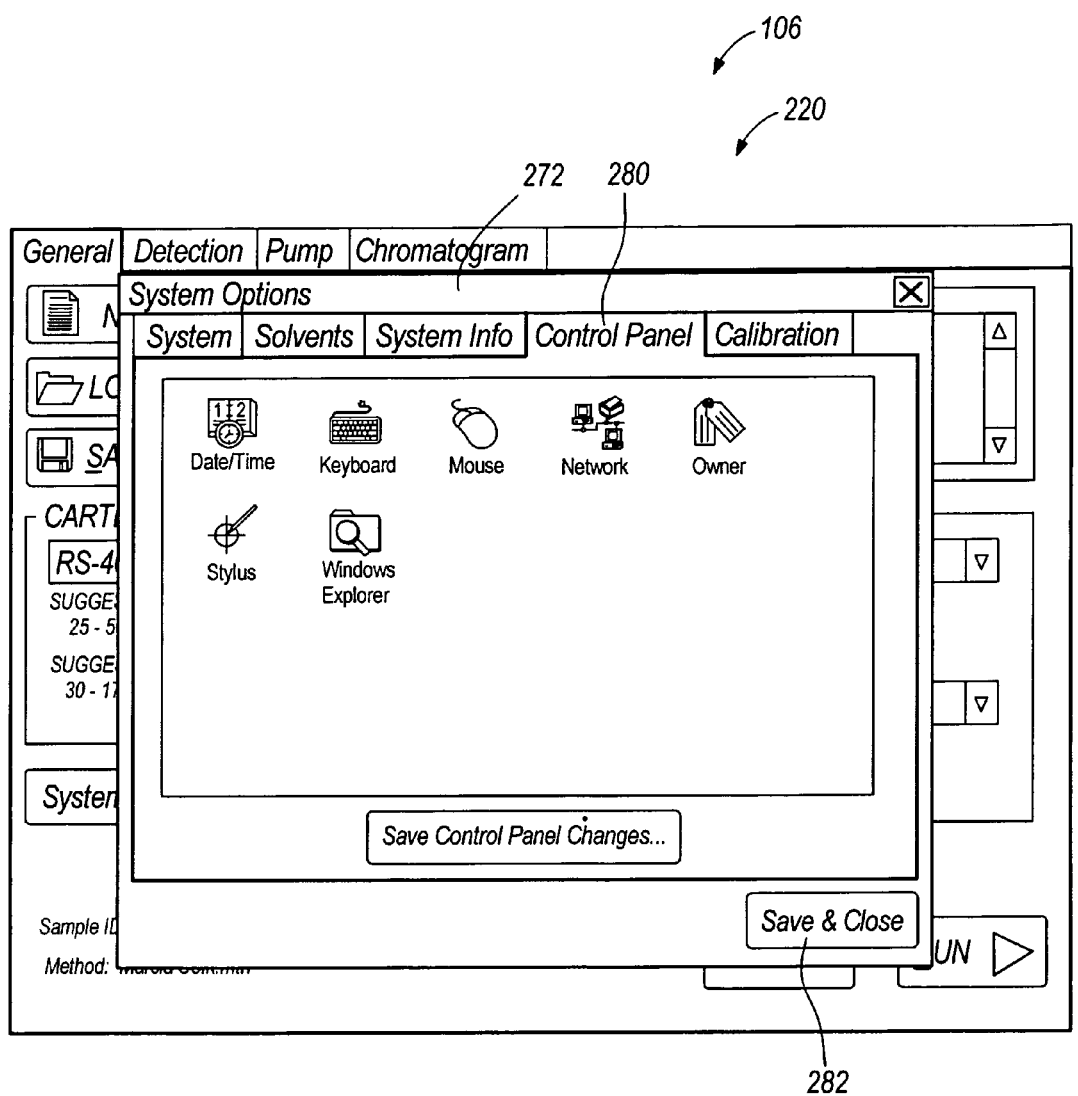

As shown in FIG. 13, the 'Control Panel' screen 280 includes a variety of Windows control panel icons, which, when selected (e.g., by double-clicking on the icon), allow access to a variety of Windows features. For example, selecting a 'Windows Explorer' icon 446 allows the user to access a Window desktop. By way of further example, selecting a 'Stylus' icon 448 opens a calibration window for calibrating the touch screen 138. Other standard Windows control panel function icons can be added to the 'Control Panel' screen 280 without departing from the spirit and scope of the present invention.

Figure 13B:
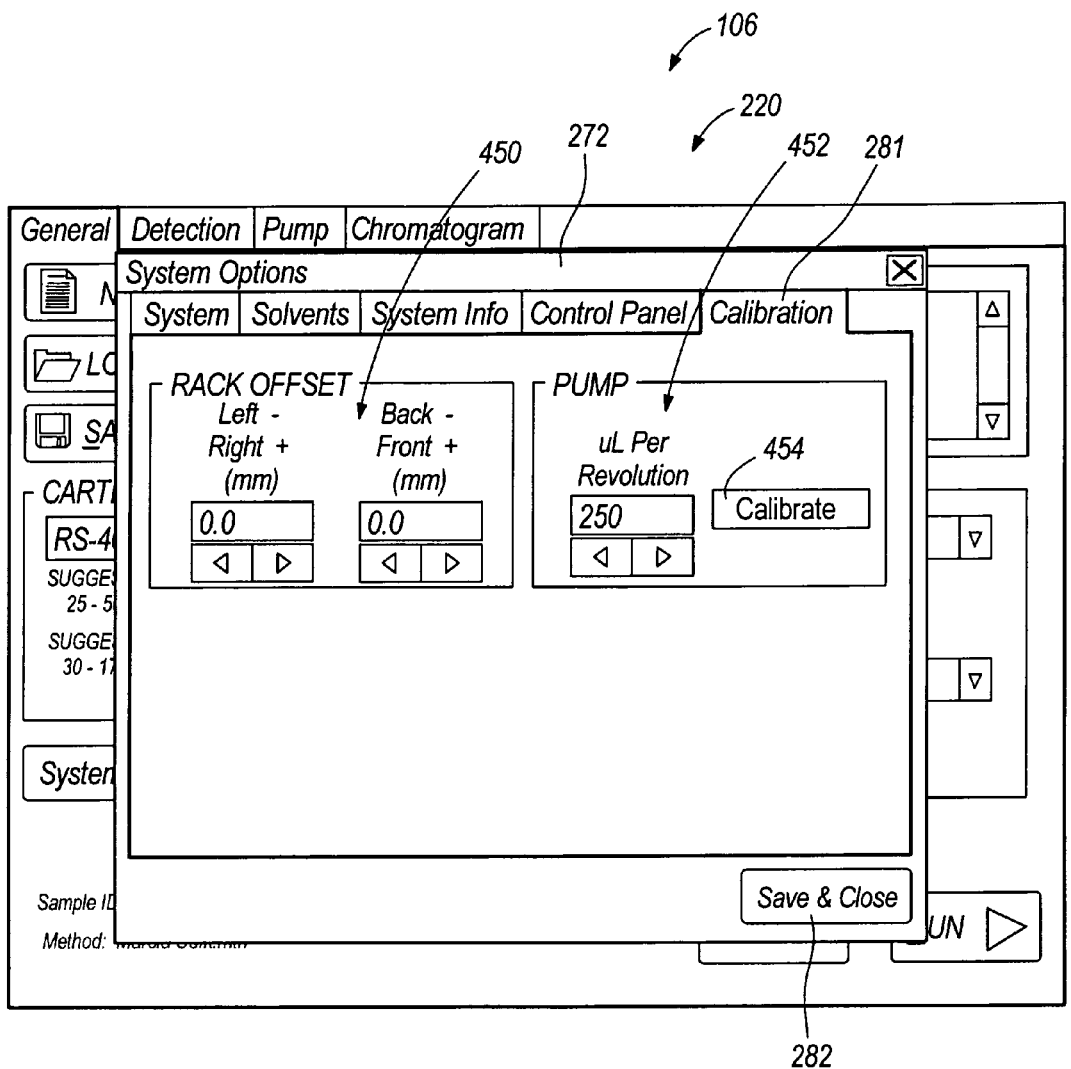

As shown in FIG. 13B, the 'Calibration' screen 281 includes a 'Rack Offset' field 450 and a 'Pump' field 452. The 'Rack Offset' field 450 allows a user to adjust the position of the fraction collector 124 relative to collection vessels 126 positioned in a collection vessel stand 128 (i.e., perform x-y calibration of the fraction collector 124), by changing the left-right position of the fraction collector 124 and the back-front position of the fraction collector 124 to prevent loss of any portion of the sample 101, and to ensure that any fraction dispensed from the second outlet 190 of the divert valve 184 of the fraction collector 124 is adequately collected in a collection vessel 126. Such a calibration may be necessary for a variety of reasons. For example, if the collection vessels 126 and/or the collection vessel stand 128 used are slightly outside of their manufacturing tolerances, or include slight defects, the x-y calibration of the fraction collector 124 may be necessary.

The 'Pump' field shows a volume per resolution value for the pump 114 connected to the chromatography system 100. In some embodiments, the user can enter or select this value. The user can then select a 'Calibrate' button 454, which sends information to firmware in the pump 114 to tell the pump 114 its volume per revolution. In some embodiments, firmware from the pump 114 tells the controller 104 what its volume per revolution is, and this value is displayed.

Figure 14:
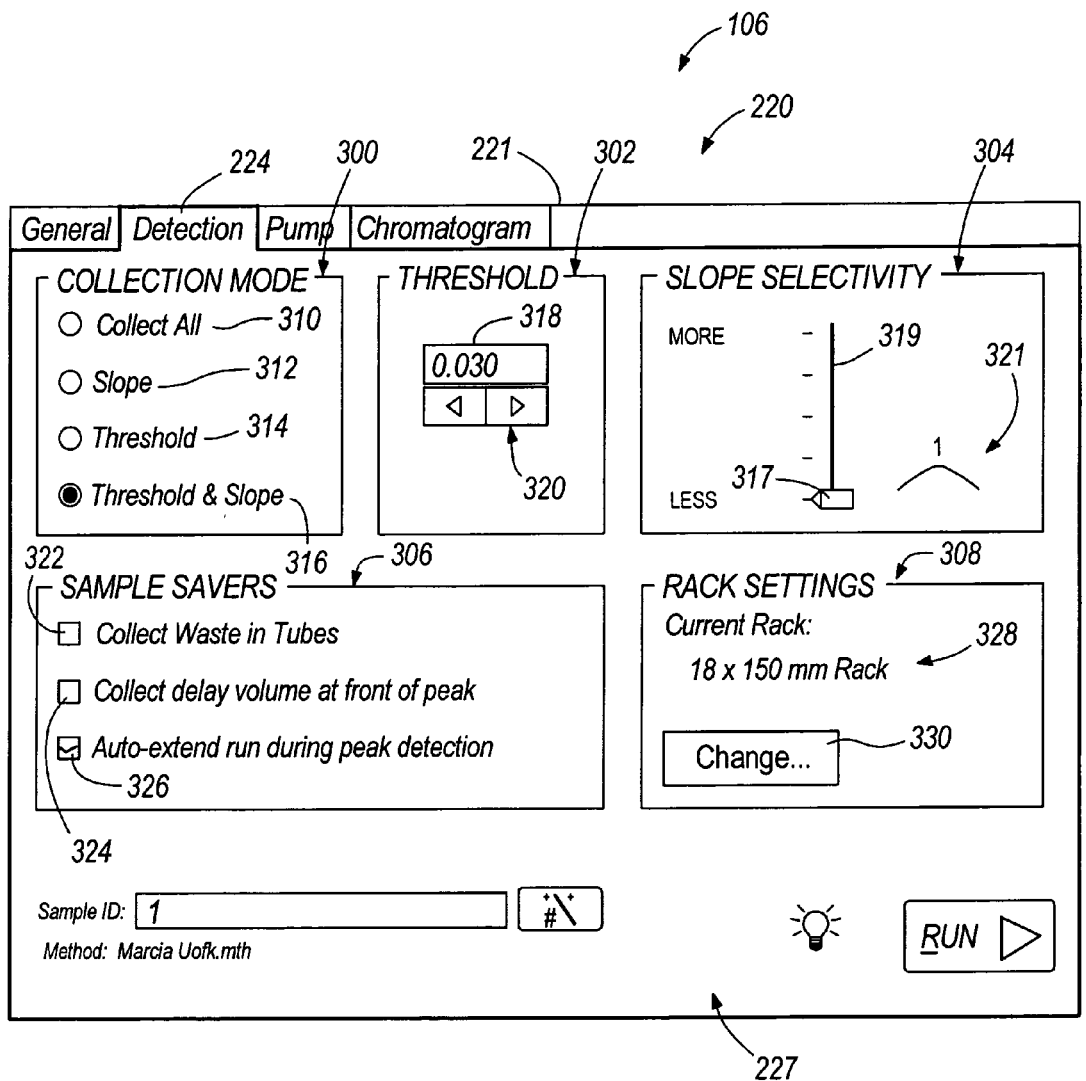

FIG. 14 illustrates the 'Detection' screen 224 according to one embodiment of the invention. The 'Detection' screen 224 includes a 'Collection Mode' field 300, a 'Threshold (AU)' field 302, a 'Slope Selectivity' field 304, a 'Sample Savers' field 306, and a 'Rack Settings' field 308.

Figure 14B:
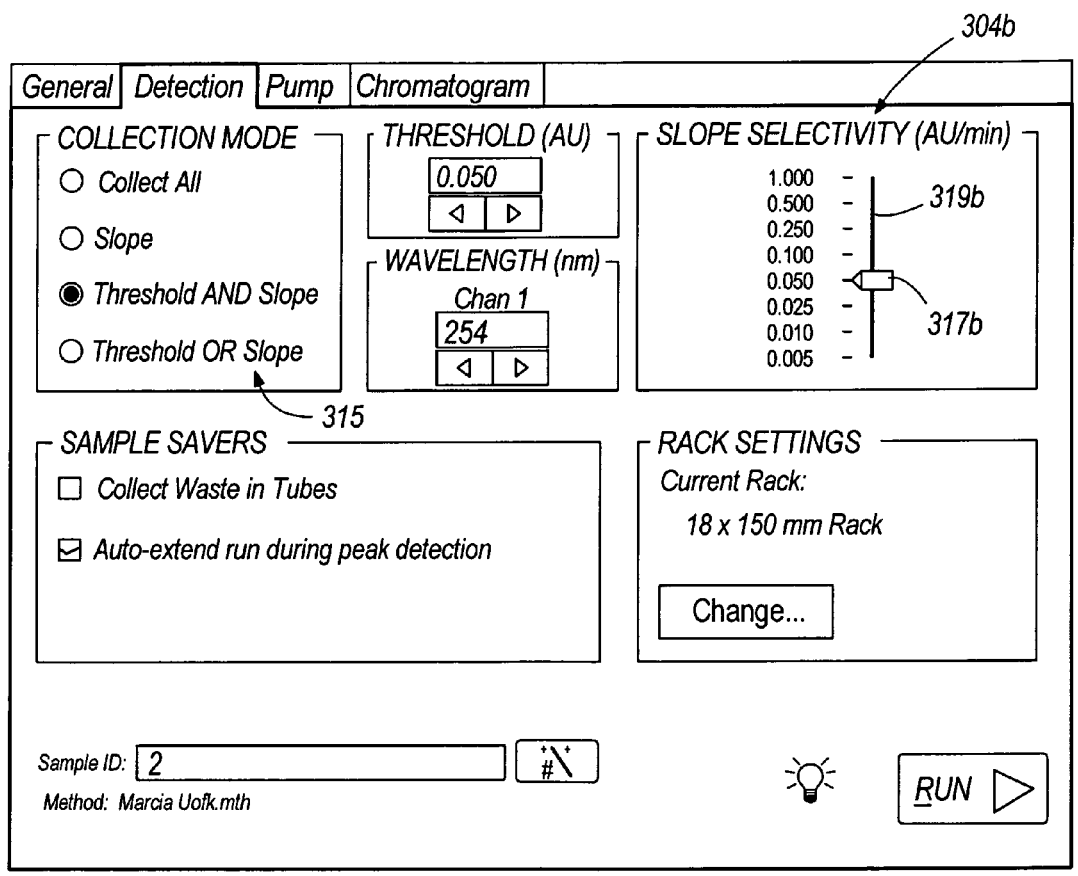

The 'Collection Mode' field 300 includes four fraction collection mode options, one of which can be selected by a user: a 'Collect All' mode 310, a 'Slope' mode 312, a 'Threshold' mode 314, and a 'Threshold & Slope' mode 316. In some embodiments, a 'Threshold or Slope' mode 315, as shown in FIG. 14B, can be selected. The 'Collect All' mode 310 allows all of the fractions of the sample 101 to be collected without being separated, so that the sample 101 is analyzed by the chromatography process and expelled to the collection vessels 126 afterward.

The 'Slope' mode 312 uses the slope of a curve on a chromatogram 318 (described below) of the fractions to determine when to separate the fractions. For example, if the slope of the curve decreases below a certain value, it may signal a break, or a boundary, between adjacent fractions, so the fraction collecting software will separate the fraction after the slope decreases below the predetermined amount. The controller 104 and/or the fraction collecting software can then signal the fraction collector 124 to stop dispensing the fraction to a collection vessel 126 and begin dispensing to waste. By way of further example, if the slope of the curve increases again above a certain value, it may signal the beginning of a new fraction, and the controller 104 and/or fraction collecting software can signal the fraction collector 124 to stop pumping and switch the divert valve 184 to a "Drain" or "Waste" position (i.e., corresponding with the first outlet 188), and move to a new collection vessel 126. The divert valve 184 can then be switched back to a "Collect" position (i.e., corresponding with the second outlet 190) when the carriage 196 is positioned over a new collection vessel 126, and the pumping can be resumed.

In some embodiments, the 'Slope' mode 312 monitors the incoming signal from the detector 122 as discrete data points. The slope (in AU/min) is calculated between adjacent points. The slope at each new incoming discrete data point is compared to a collection of previous data points (e.g., a rolling average, etc.) to determine if the slope at the new data point passes a comparison test (e.g., if the slope at the new incoming data point exceeds that of the previous six points by a certain amount, etc.). In some embodiments, a plurality of tests can be performed for each new data point, and the tests can be weighted to calculate a total score for the new data point. The total score can be compared to some threshold value to determine if the new data point is part of a continuing peak, if the new data point is going out of a peak, or if the new data point is part of a new peak, etc.

In some embodiments, the 'Slope' mode 312 computes the slope between a first new data point and a prior data point, and stores this as 'Slope 1,' for example. The 'Slope' mode 312 then computes the slope between a second new data point and the first new data point, and stores this as 'Slope 2.' Slope 2 and Slope 1 are then compared to determine if the new data point is part of a continuing peak, going out of a peak, or part of a new peak, etc.

The 'Slope Selectivity' field 304 can be used to adjust how the fraction collecting software will select peaks or ignore peaks. The 'Slope Selectivity' field 304 includes a sliding indicator 317 that can be moved between 'More' and 'Less' selective positions on an axis 319. Moving the sliding indicator 317 along the axis 319 to different steps along the axis 319 chooses a different set of parameters for various tests that are performed for peak selection based on slope. Accordingly, if a user wishes to collect more fractions (i.e., be "less selective"), he/she can slide the sliding indicator 317 using the stylus 140 or a fingertip to a lower position on the axis 319 to collect more fractions, even those having subtle peaks on the chromatogram. Accordingly, the fraction collecting software will signal the fraction collector 124 to send more fractions of the sample 101 to the collection vessels 126, and fewer to waste. On the other hand, if a user wishes to collect fewer fractions (i.e., be "more selective"), he/she can slide the sliding indicator 317 to a higher position on the axis 319 to collect only the fractions having well-defined peaks on the chromatogram. Accordingly, the fraction collecting software will signal the fraction collector 124 to send fewer fractions of the sample 101 to the collection vessels 126, and more to waste. A peak display 321 illustrates an example of a peak corresponding to each position along the axis 319.

In some embodiments, the 'Slope Selectivity' field 304 is replaced with a 'Slope Sensitivity' field 304b, as shown in FIG. 14B, and the sliding indicator 317b is movable along the axis 319b, which is defined in units of absorbance units (AU)/min. In some embodiments, as shown in FIG. 14B, the axis 319b runs from a lower position of 0.005 AU/min. to an upper position of 1.000 AU/min., in increments of 0.005 AU/min.

The 'Threshold' mode 314 uses a baseline threshold value to determine if a fraction is worth collecting or should be dispensed to waste. For example, if a portion of the curve of the chromatogram representing the sample 101 is below a threshold value (in absorbance units (AU)), the controller 104 and/or the fraction collecting software will direct the fraction collector 124 to dispense the fraction of the sample 101 corresponding to that portion of the curve to waste. By way of further example, if a portion of the curve of the chromatogram is above a threshold value of absorbance units, the controller 104 and/or the fraction collecting software will direct the fraction collector 124 to dispense the fractions to the collection vessels 126 until the curve goes below the threshold value again. Thus, any fraction of the sample 101 corresponding to a portion of the chromatogram that is above a predetermined threshold of absorbance units will be collected. However, the fractions will be collected together, and will not be separated. The threshold value, in absorbance units (AU), can be specified in the 'Threshold (AU)' field 302. A user can use the keyboard 130 to type a value into a threshold text field 318, or a user can use incrementing buttons 320 to increase or decrease the value displayed in the text field 318. In some embodiments, the threshold value defaults to 0.100 AU.

The 'Threshold & Slope' mode 316 includes a combination of the 'Slope' mode 312 and the 'Threshold' mode 314. The 'Threshold & Slope' mode 316 will only collect fractions that correspond to portions of the chromatogram that are above a predetermined threshold value, and the fraction collector 124 will separate the fractions and dispense each fraction into a new collection vessel 126. The fraction collecting software will separate the fractions based on the slope of the chromatogram, as described above.

The 'Threshold or Slope' mode 315 determines that fractions will be collected if the parameters for the 'Threshold' collection mode are met or if the parameters for the 'Slope' collection mode are met.

The 'Sample Savers' field 316 includes three checkboxes: a 'Collect Waste in Tubes' checkbox 322, a 'Collect delay volume at front of peak' checkbox 324, and an 'Auto-extend run during peak detection' checkbox 326. By checking the 'Collect Waste in Tubes' checkbox 322, the user specifies that all "non-peak" portions of the sample 101 (i.e., portions of the sample 101 that are not detected by the detector 122 as absorbing any radiation) will be collected, and not sent a waste container. In some embodiments, collection vessels 126 can be identified as containing "waste" or "non-peak" material, and the fraction collector 124 can be controlled to move to those collection vessels 126. For example, in some embodiments, collection vessels 126 for collecting "non-peak" material can be designated with black circles.

By checking the 'Collect delay volume at front of peak' checkbox 324, the user decides to collect a portion of a fraction corresponding to when the detector 122 first noticed an increase in absorbance in radiation. In many cases, the most pure (i.e., most desirable) portion of a fraction of the sample 101 corresponds to a point in time where the detector 122 first notices an increase in absorbance of radiation, which corresponds to a front of a peak on a chromatogram 370 (described below in greater detail). Because a slope calculation needs more than one data point to determine the slope of the absorbance detected by the detector 122, the slope can be calculated by comparing a new absorbance data point with a prior data point. If the 'Collect delay volume at front of peak' checkbox 324 is checked, and a sufficiently increasing slope (based on the settings of the fraction collecting software) has been found, the fraction collecting software determines where the slope was first increasing by checking previous slope calculations, and controls the fraction collector 124 to collect a fraction beginning from that point. Specifically, the "delay volume" refers to the volume of fluid in the fluid path 112 between the outlet 176 of the flow cell 170 of the detector 122 to the inlet 186 of the divert valve 184 on the fraction collector 124. The delay volume can be calculated by knowing the length of tubing (or similar) used to connect the outlet 176 to the inlet 186, and the cross-sectional area of that tubing. In some embodiments, the chromatography system 100 is defaulted to send the delay volume at the front of a peak that identifies a fraction to waste and continue collecting a volume of fluid equal to the delay volume when collecting the fraction at the back of the peak to ensure that the entire fraction is collected. By checking the 'Collect delay volume at front of peak' checkbox 324, this default is overridden, and the delay volume is not sent to waste.

By checking the 'Auto-extend run during peak detection' checkbox 326, the user is telling the chromatography system 100 that if the fraction collecting software has determined that the fraction collector 124 should be collecting a fraction when the run time for the chromatography run expires, the run should continue, and the fraction collector 124 should continue dispensing the fraction to a collection vessel 126 until the fraction collecting software determines that the entire fraction has been collected, based on whichever collection mode is being used.

The 'Rack Settings' field 308 includes a 'Current Rack:' field 328, which displays the collection vessel stand 128 that is currently positioned in the recess 202 of the housing 102 for collecting fractions of the sample 101. The 'Rack Settings' field 308 further includes a 'Change . . . ' button 330. Selecting the 'Change . . . ' button opens a 'Rack Settings' window 332, as shown in FIG. 15.

Figure 15:
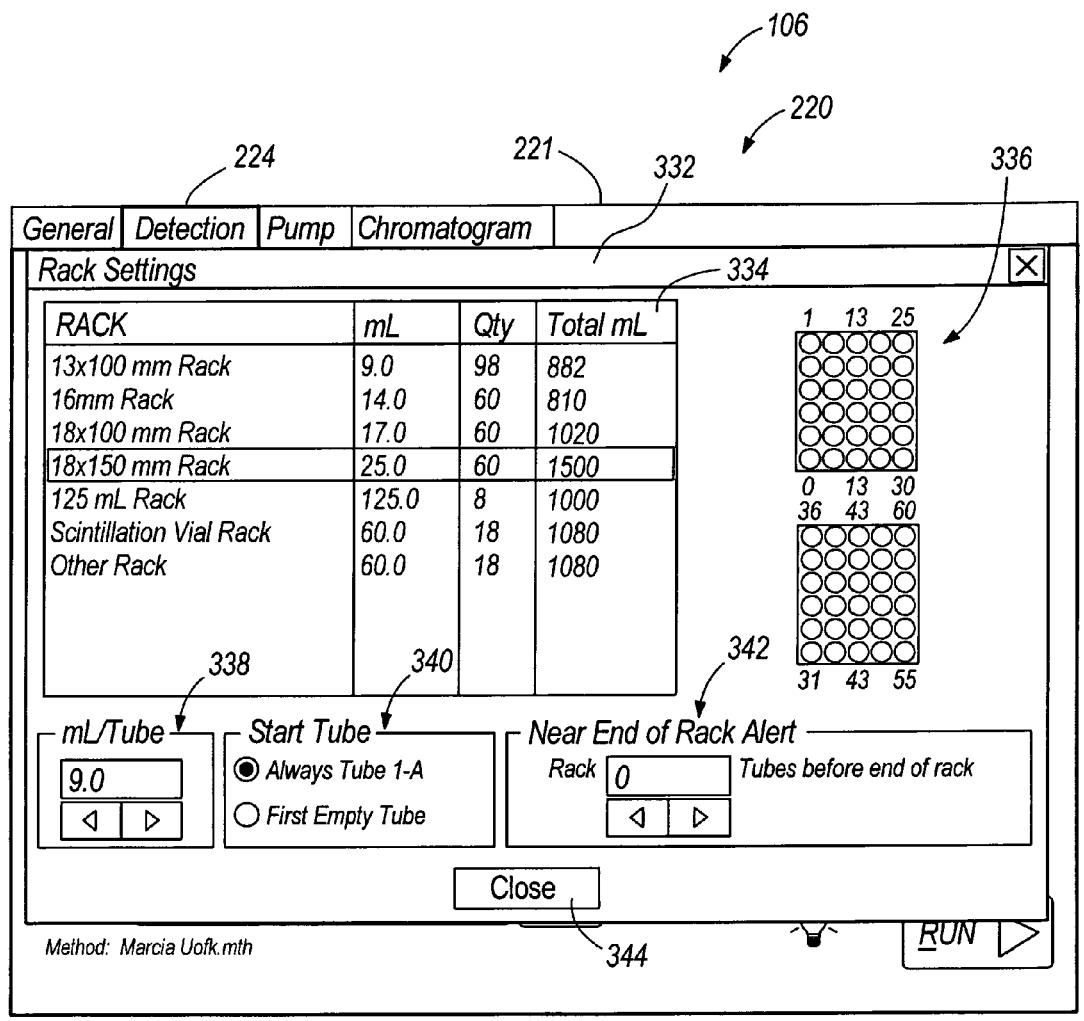

FIG. 15 illustrates one embodiment of the 'Rack Settings' window 332, which includes a spreadsheet 334 of collection vessel stand 128 information and specifications and from which a user can highlight a collection vessel stand 128 of choice. A rack display 336 illustrates the rack that is currently highlighted in the spreadsheet 334. The user can add rows to the spreadsheet, edit the spreadsheet or delete rows from the spreadsheet to suit his/her needs. Alternatively, in some embodiments, the collection vessel stand 128 selection can be completed in a manner similar to the manner in which the cartridge 120 and the solvents 115 are selected, including a drop-down menu list that can be modified by accessing a configurable text file. For example, in such embodiments, a collection vessel stand configurable text file can be accessed by selecting the 'System Options . . . ' button 270 on the 'General' screen 222. Regardless of whether the collection vessel stand options are listed in a spreadsheet or a configurable text file (which can be in a table format), the list can include a variety of data relating to the collection vessel stands 128, including, without limitation, at least one of the following: an ID no.; number of rows (i.e., if the collection vessel stand 128 is configured as a grid); number of columns; maximum number of collection vessels 126 that can be held; position or distance data relating to the relative positions of the collection vessels 126 in the rack and/or the position of the collection vessel stand 128 in relation to the recess 202 of the housing 102 or the fraction collector 124; cap volume (e.g., in mL); display description (i.e., the name given to the rack, which may be used in a drop-down menu, for example); and travel type (e.g., a "0" in a 'travel type' field may refer to a serpentine travel path, meaning the fraction collector 124 would increment through the collection vessel stand 128 by going down, over, up, over, down, and so on; a "1" may refer to a travel path where the fraction collector 124 increments through the collection vessel stand 128 by going down one column, down the next column, and so on; etc.).

The 'Rack Settings' window 332 further includes a 'mL/Tube' field 338, which allows the user to select a desired size of collection vessel 126, and a 'Start Tube' field 340, which allows the user to select whether the fraction collector 124 should begin dispensing fractions in the collection vessel 126 positioned in the first position of the collection vessel stand 128, or if the fraction collector 124 should begin dispensing fractions in the first empty collection vessel 126.

The 'Rack Settings' window 332 further includes a 'Near End of Rack Alert' field 342, which allows a user to program the chromatography software to alert him/her when the fraction collector 124 is a certain number of collection vessels 126 from the end of what is available in the collection vessel stand 128. The user can specify the number of collection vessels 126 prior to the end of the collection vessel stand 128 he/she would like to be alerted. The alert can include any combination of a variety of audible and visible alerts. Visible alerts can be displayed on one or more of the LCD screen 134 on the touchpad 132, or the monitor 136.

The 'Rack Settings' window 332 further includes a 'Close' button 344, which can be selected when the user accepts or has completed the information in the 'Rack Settings' window 332. Selecting the 'Close' button 344 will return to the 'Detection' screen 224.

Figure 16:
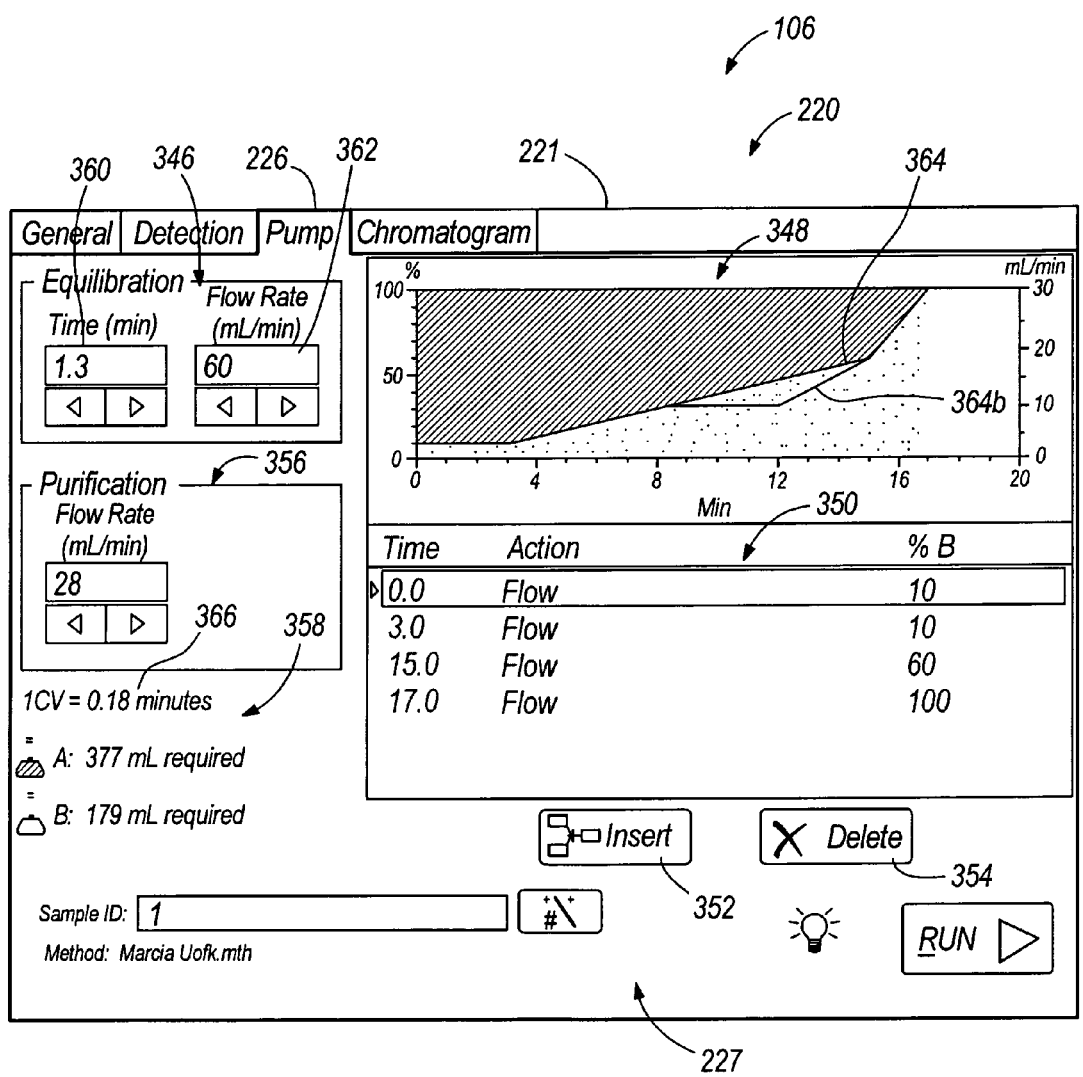

FIG. 16 illustrates the 'Pump' screen 226 according to one embodiment of the present invention. The 'Pump' screen 226 includes an 'Equilibration' field 346; a solvent gradient display chart 348; a solvent gradient spreadsheet 350 including an 'Insert' button 352 for inserting a row into the spreadsheet 350 and a 'Delete' button 354 for deleting a row in the spreadsheet 350; a 'Purification' field 356, and a required solvent volume field 358.

The 'Equilibration' field 346 includes a 'Time' text field 360 and a 'Flow Rate' text field 362, which allow a user to enter a time and flow rate, respectively, for equilibration of the chromatography system 100. An equilibration of the cartridge 120 will begin when a chromatography run is begun. Equilibrating the cartridge 120 and the chromatography system 100 is well-known in the art and therefore will not be discussed in greater detail below.

The solvent gradient spreadsheet 350 allows a user to define a solvent gradient 364 for a chromatography run. By filling out a row in the solvent gradient spreadsheet 350, the user enters a point in time in the chromatography run, an action at that point in time, and a percent of one solvent 115 at that point in time. By entering several rows, a user can define the relative amounts of the solvents 115 at given points in time throughout a chromatography run to define the solvent gradient 364, which is displayed in the solvent gradient display chart 348. For example, as shown in FIG. 16, solvent B is present at 10% for the first three minutes of the run, then increases linearly to 60% at the fifteen-minute mark of the run, and then increases linearly to 70% at the seventeen-minute mark of the run.

The required solvent volume field 358 automatically updates based on the solvent gradient 364 that is generated to tell the user how much of each solvent 115 will be required to complete the chromatography run. The required solvent volume field 358 also includes a cartridge volume (or 'column volume'; 'CV') flow rate field 366. As is well-known in the art, CV is the amount of mobile phase that fits in a packed cartridge 120. Accordingly, CV flow rate is a flow rate (e.g., CV/min.) based on the flow rate of the pump 114 (e.g., in mL/min), and the CV value associated with the selected cartridge 120 (e.g., data automatically entered after selection of the cartridge 120 that can be stored in the cartridges configurable text file). Some users may wish to work in CV rate, rather than pump flow rate. The CV flow rate field 366 tells how much time (e.g., in minutes) it will take for the mobile phase to pass through one cartridge 120, based on the CV flow rate.

Figure 17:
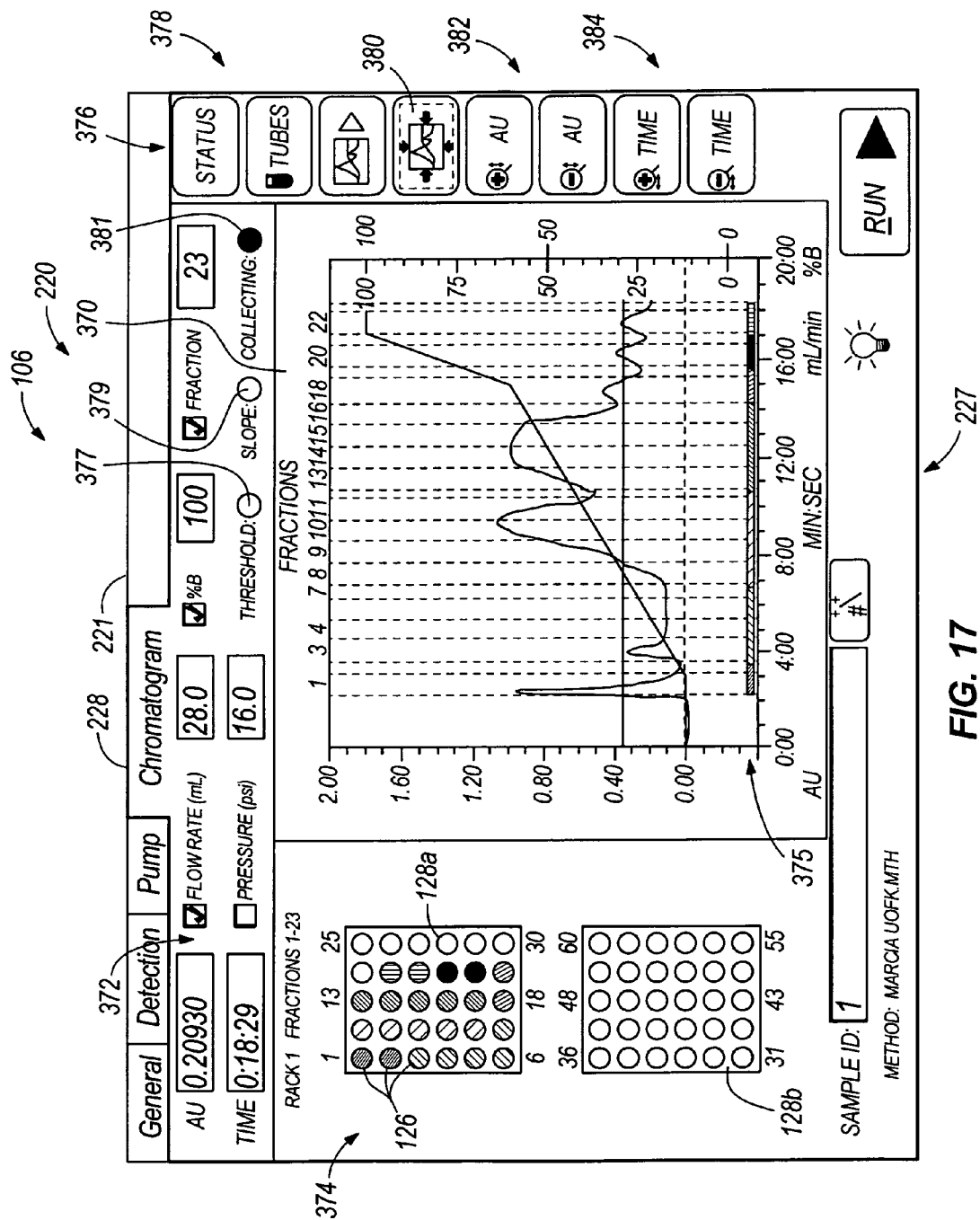

FIG. 17 illustrates the 'Chromatogram' screen 228 according to one embodiment of the present invention. The 'Chromatogram' screen 228 displays a chromatogram 370 for a chromatography run as it is generated during the run, and after the run is completed. The 'Chromatogram' screen 228 includes status bar 372 that displays the values for various parameters at a given point in time. Some of the values displayed in the status bar 372 can be selected to be displayed in the status bar 372 or not by selecting or deselecting corresponding checkboxes. The values that can be displayed in the status bar 372 include absorbance units, time, flow rate, pressure, % second solvent $115b$, a number corresponding to which fraction of the sample 101 is being charted in the chromatogram.

The status bar 372 further includes a 'Threshold' indicator 377, a 'Slope' indicator 379, and a 'Collecting' indicator 381. Each indicator 377, 379, 381 has three states: Green: triggered, Red: not triggered, and Gray: inactive. If the collection mode chose includes both of the threshold mode and the slope mode, both corresponding indicators 377, 379 will be active. The 'Slope' indicator 379 is triggered and turns green when the chromatogram 370 begins to rise quickly enough, based on the 'Slope Selectivity' parameters selected in the 'Detection' screen 224. When the fraction collecting software has determined that the peak has passed, the 'Slope' indicator 379 is no longer triggered and turns to red. Similarly, the 'Threshold' indicator 377 turns green when the chromatogram 370 reaches or exceeds the threshold absorbance unit that was set in the 'Threshold (AU)' field 302 in the 'Detection' screen 224. Whenever the chromatogram falls below this threshold value, the 'Threshold' indicator 377 turns red. The 'Collecting' indicator 381 turns green when the fraction passing through the detector 122 will be collected, as determined by the fraction collecting software. The actual collection is delayed until the fraction reaches the divert valve 184 of the fraction collector 124. The 'Collecting' indicator 381 will turn green some time before the divert valve 184 switches to the second outlet 190.

The 'Chromatogram' screen 228 further includes a graphic rack display 374 of the collection vessel stands 128 being used. The graphic rack display 374 is dynamic and color-coded such that the fraction of the sample 101 in each collection vessel 126 in the collection vessel stand 128 can be matched up with a similarly-colored color band 375 displayed in a lower portion of the chromatogram 370 to visually determine which fraction is in which collection vessel 126. Such 'fraction mapping' allows facile retrieval of a particular fraction of interest for storage or further analysis. Color-coding fraction mapping can be accomplished using a variety of software tools to match up the collection vessels 126 with the corresponding portions of the chromatogram 370. For example, FRACTRAC™ fraction mapping software (available from Analogix, Inc., Burlington, Wis.) can be used for this purpose. Other types of matching or coding can be used in addition to color-coding without departing from the spirit and scope of the present invention, including, without limitation, patterns, shading, etc.

As shown in FIG. 17, a fraction can take up more than one collection vessel 126. In such embodiments, the user may wish to consolidate all of the collection vessels 126 pertaining to one fraction into one container. In some embodiments, the chromatography system 100 allows for automatic consolidation of fractions. This could be set to be performed automatically after the completion of a run, or a user could instruct the chromatography system 100 (e.g., via the graphical user interface 106) to consolidate the fractions. For example, after a run, the user can instruct the chromatography system 100 to take all of the collection vessels 126 pertaining to a first fraction and consolidate them into one larger vessel. By way of further example, perhaps the user is not interested in keeping a second fraction, so he/she can instruct that the contents of all of the collection vessels 126 pertaining to the second fraction be sent to waste, and so on. Finally, the user can dispose of all of the used and empty collection vessels 126 (or, in some embodiments, the chromatography system may wash the collection vessels 126 for reuse). Consolidation of the fractions by the chromatography system 100 can save the user from having to perform all of the liquid handling steps manually, which can be tedious and time-consuming.

The 'Chromatogram' screen 228 further includes display manipulation buttons 376. In some embodiments, the display manipulation buttons 376 include toggle buttons 378 to control whether the status bar 372, chromatogram 370 and/or graphic rack display 376 are displayed. The display manipulation buttons 376 further include a chromatogram size adjustment button 380 that can increase or decrease the amount of the 'Chromatogram' screen 228 that is taken up by the chromatogram 370. The display manipulation buttons 376 further include absorbance unit zoom buttons 382 for zooming in and out on the y-axis of the chromatogram 370, and time zoom buttons 384 for zooming in and out on the x-axis of the chromatogram 370.

Figure 18:
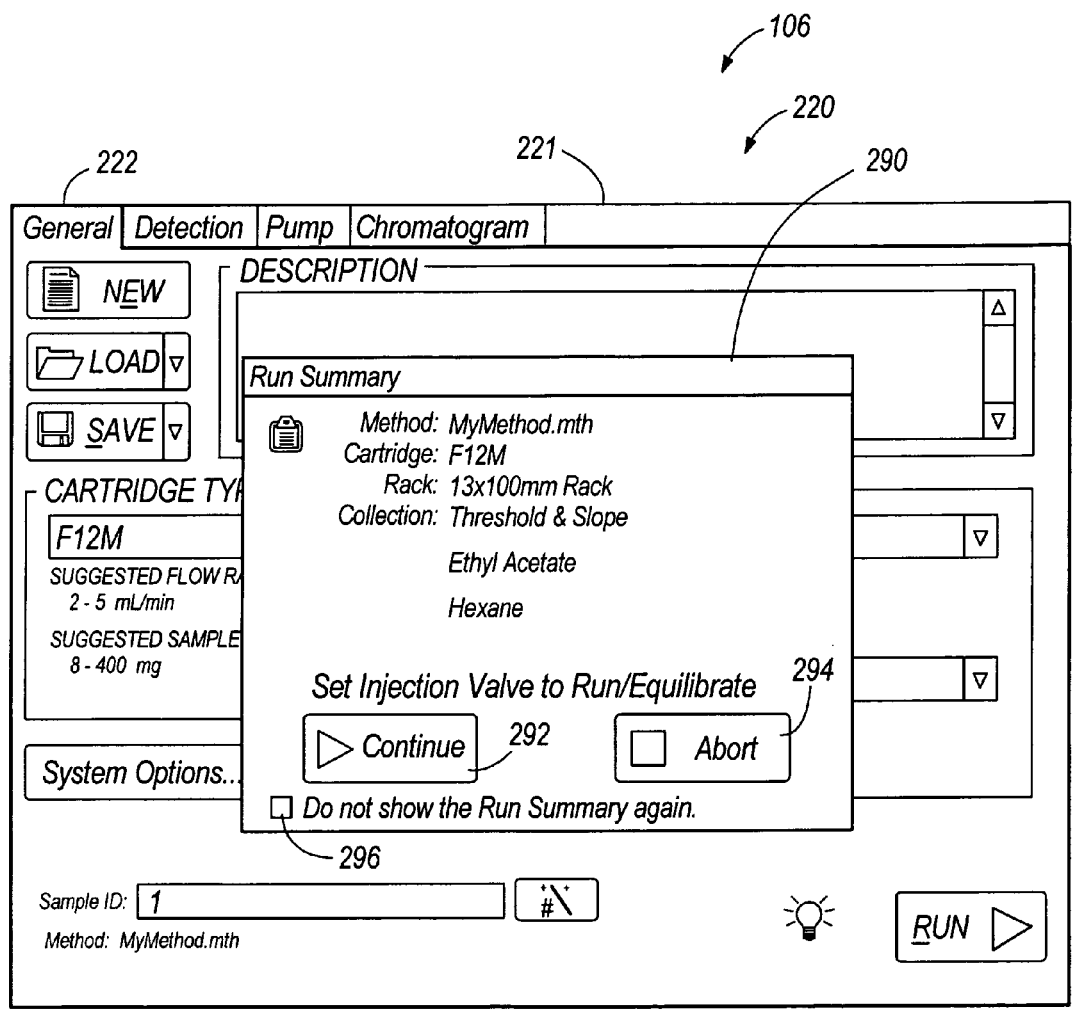

As described above, the static region 227 of the main window 221 is accessible from any of the four screens 222, 224, 226, 228 and includes the 'Run' button 230. As shown in FIG. 18, the first time the 'Run' button 230 is selected, a 'Run Summary' window 290 will open to display a summary of the method about to be run on the chromatography system 100. In some embodiments, as shown in FIG. 14, the summary includes the title of the method file, the cartridge type, the collection vessel stand 128 chosen, the fraction collection mode chosen, and the solvents 115 chosen. The 'Run Summary' window 290 can further include a 'Continue' button 292 to begin the chromatography run (or to begin equilibrating the chromatography cartridge 120), an 'Abort' button 294 to abort the chromatography run, and a 'Do not show the Run Summary again' checkbox 296. If the 'Do not show the Run Summary again' checkbox 296 is checked, a chromatography run can be started by simply selecting the 'Run' button 230, and the 'Run Summary' window 290 will not open prior to beginning the chromatography process.

Figure 19:
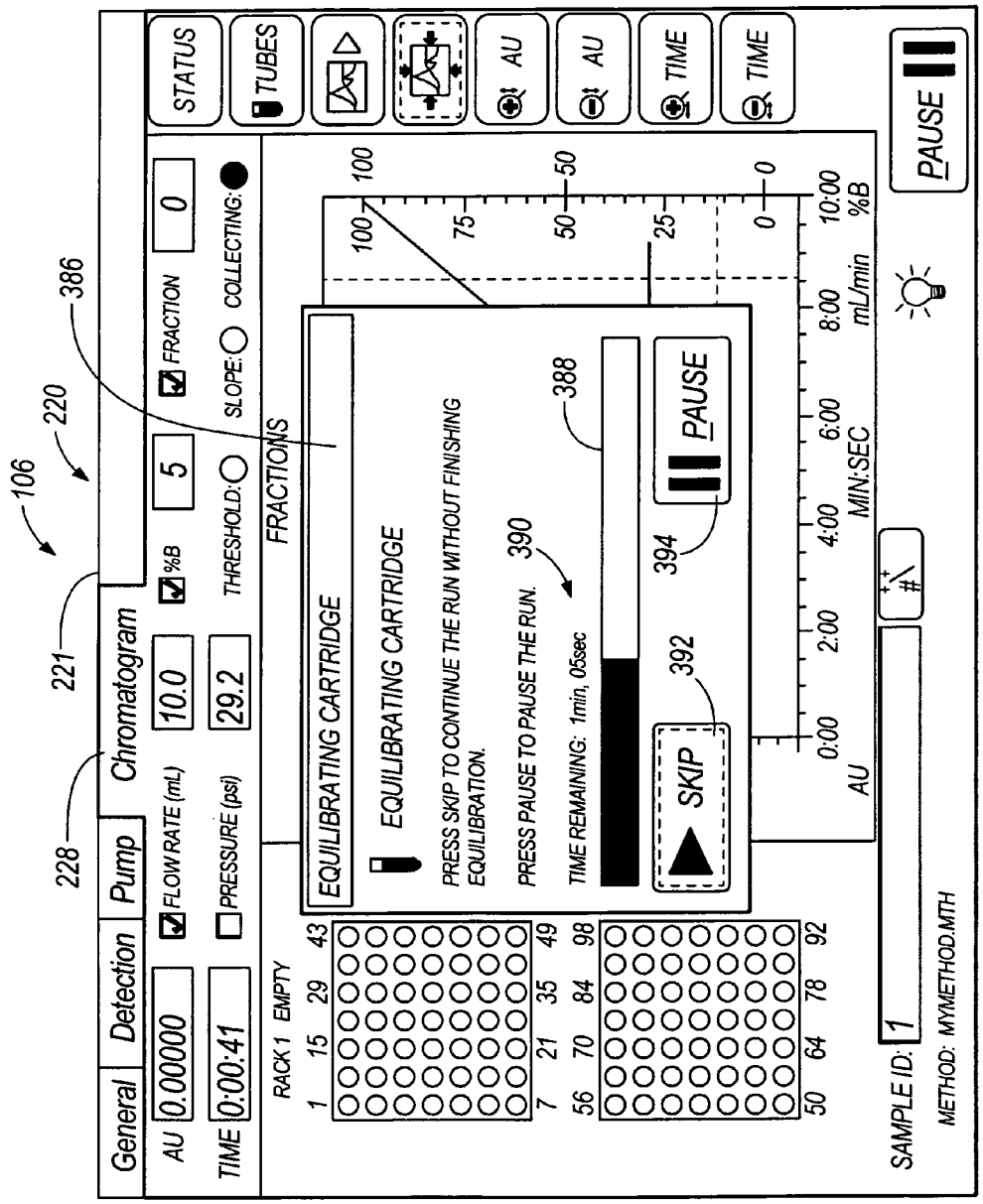

If the 'Continue' button 292 is selected in the 'Run Summary' window 290, an 'Equilibrating Cartridge' window 386 will open, as shown in FIG. 19, and the chromatography system 100 will begin equilibrating the chromatography cartridge 120. The 'Equilibrating Cartridge' window 386 includes a time progression bar 388 and a 'Time Remaining' text field 390 to visually display the progress of equilibration. The 'Equilibrating Cartridge' window 386 further includes a 'Skip' button 392, which, when selected, allows the chromatography run to begin without completing equilibration, and a 'Pause' button 394, which, when selected, allows at least one of the equilibration and the chromatography run to be paused. After the 'Pause' button 394 is selected, a 'Resume' button (such as the 'Resume' button 404 shown in FIG. 20, described below) and an 'Abort' button (such as the 'Abort' button 406 shown in FIG. 20, described below) will appear, and the user can then select whether he/she wishes to continue running the chromatography process, or whether he/she wishes to abort the run.

When the 'Continue' button 292 of the 'Run Summary' window 290, or simply when the 'Run' button 230 is selected (e.g., when the 'Do not show the Run Summary again' checkbox 296 has been checked in the 'Run Summary' window 290), the 'Run' button 230 changes to a 'Pause' button 295, as shown in FIG. 19. The 'Pause' button 295 can be selected at any time throughout the chromatography process to pause the run. By pausing the run using the 'Pause' button 295, the user can edit any of the method file and run settings "on-the-fly" before resuming the chromatography run. Such "on-the-fly" editing provides flexibility in the chromatography process and eliminates errors and wasted chromatography runs by allowing the run to be paused and edited before an error occurs. The 'Pause' button 295 in the graphical user interface 106 is only one way to implement "on-the-fly" editing. The chromatography run can be paused using a variety of other means, including, without limitation, a 'Pause' button on the touchpad 132, etc.

Figure 20:
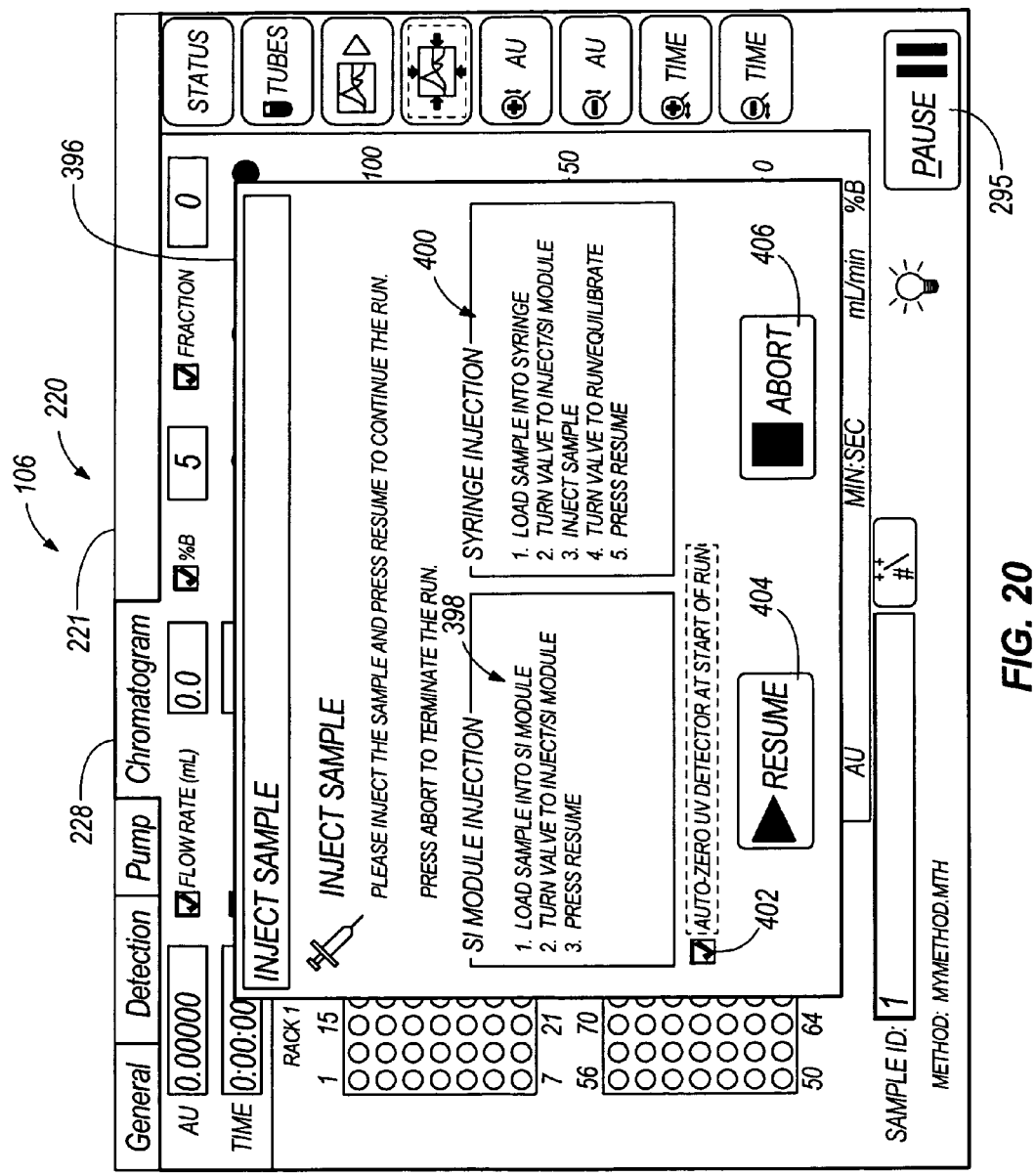

As shown in FIG. 20, an 'Inject Sample' window 396 will open when either the 'Skip' button 392 is selected, or the cartridge 120 is finished equilibrating. The 'Inject Sample' window 396 includes a 'SI Module Injection' instructions field 398 and a 'Syringe Injection' instructions field 400, which each include instructions for injecting the sample 101 using the sample injector 116. Alternatively, as described above, the sample 101 can be loaded directly into the inlet 119 of the cartridge 120.

The 'Inject Sample' window 396 further includes an 'Auto-zero UV detector at start of run' checkbox 402. If the 'Auto-zero UV detector at start of run' checkbox 402 is checked, the detector 122, whether it is a UV detector or another type of detector 122, will be zeroed (i.e., the baseline absorbance reading will be zeroed) before proceeding with the chromatography run. The 'Inject Sample' window 396 further includes a 'Resume' button 404 to continue with the chromatography run, and an 'Abort' button 406 to abort the chromatography run.

Figure 21:
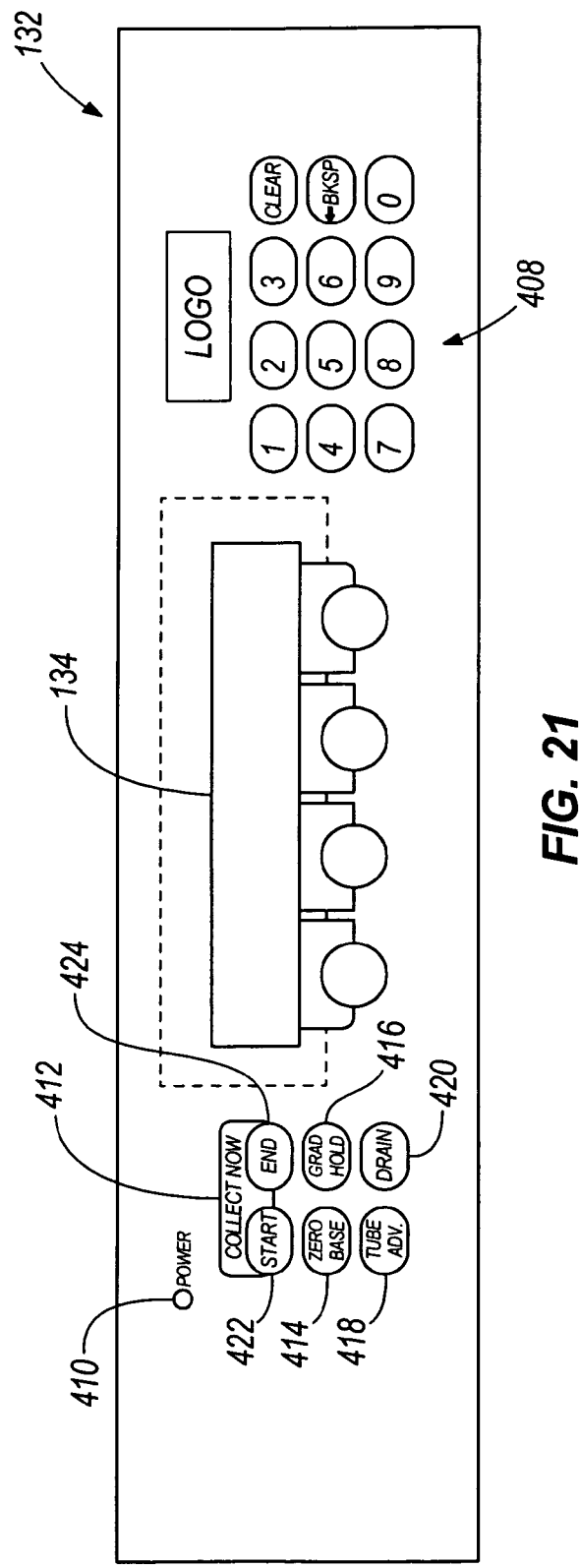
FIG. 21 is a schematic view of a touchpad according to one embodiment of the present invention.

FIG. 21 illustrates the touchpad 132 according to one embodiment of the present invention. The touchpad 132 includes the LCD screen 134, a numeric keypad 408, a power indicator 410, 'Collect Now' controls 412, a 'Zero Base' button 414, a gradient hold button 416, a tube advance button 418, and a 'Drain' button 420.

The numeric keypad 408 can be used to enter numeric data into any of the text fields in the wizard program 220, enter numeric data in or select items from menus in the LCD screen 134 on the touchpad 132, or enter numeric data in any other word processing or spreadsheet program associated with the controller 104. The numeric keypad 408 includes buttons enumerated from 0 to 9 and, a 'CLEAR' button for clearing out a field, and a 'BKSP' button for deleting the last character entered. The power indicator 410 indicates when the fraction collector 124 is powered on.

The 'Collect Now' controls 412 include a Collect Now 'Start' button 422 and a Collect Now 'End' button 424. The 'Collect Now' function allows a user to override peak detecting software and the absorbance data measured by the detector 122 to collect a fraction that appears desirable or interesting based on the chromatogram, but which normally would be sent to waste, based on the settings and the collection mode of the fraction collecting software. Pressing the Collect Now 'Start' button 422 causes the controller 104 to send a signal to the fraction collector 124, and particularly, to the divert valve 184 to send all of the fractions of the sample 101 (in some embodiments, after the delay volume has passed through the divert valve 184) out the second outlet 190 to the collection vessels 126 to be collected, no matter what data has been acquired from the detector 122. Pressing the Collect Now 'End' button 424 resumes the separation of the fractions of the sample 101 based on the settings and the collection mode of the fraction collecting software. The 'Collect Now' controls 412 can be used to make sure that the sample 101 does not go to waste, and can be used to override the fraction collecting software at the last minute, if it is determined that a mistake was made in programming the settings of the fraction collecting software. In some embodiments, the 'Collect Now' controls 412 include simply one toggle button that can be pressed once to activate the 'Collect Now' function, and can be pressed a second time to disable the 'Collect Now' function.

The 'Zero Base' button 414 allows a user to manually zero the absorbance unit baseline in the detector 122. In some embodiments, fractions from a previous sample may have been present in the flow cell 170 of the detector 122 when the detector 122 was zeroed using the wizard program 220 (i.e., by checking the 'Auto-zero UV detector at start of run' checkbox 402, as shown in FIG. 20 and described above), causing inaccurate absorbance unit measurements. In other embodiments, the 'Auto-zero UV detector at start of run' checkbox 402 may not have been checked, and the detector 122 may not have been zeroed between runs. Accordingly, the user can press the 'Zero Base' button 414 on the touchpad 132 to zero the detector 122 after priming or flushing the fluid path 112. In still other embodiments, adding a solvent 115 that, even slightly, absorbs radiation in the detector 122 during the chromatography run may artificially increase the absorbance value. The 'Zero Base' button can be pressed to compensate for this.

The gradient hold button 416 can be used to override the solvent gradient 364 that was generated using the 'Pump' screen 226 of the wizard program 220. In some cases, the user may see a peak on the chromatogram 370 of a fraction that is being collected at a given solvent concentration, and the user may wish to override the solvent gradient 364 that was originally generated to continue collection of that peak. In that case, the user may press the gradient hold button 416 to maintain a desired solvent concentration. When the user presses the gradient hold button 416 a second time, the solvent concentration will resume following the originally generated solvent gradient 364. For example, with respect to the solvent gradient 364 shown in FIG. 16, if the user determined at the 8-minute mark to hold the solvent concentration at about 30% of the second solvent 115$b$ (% B in FIG. 16), he/she would push the gradient hold button 416 at the 8-minute mark, and the solvent gradient would follow a new curve, namely, a modified solvent gradient 364$b$. According to the modified solvent gradient 364$b$ shown in FIG. 16, the user pressed the gradient hold button 416 again at the twelve-minute mark. After the gradient hold button 416 is pressed a second time, the solvent concentration resumes following the generated solvent gradient 364 by increasing from 30% B to 50% B within 3 minutes, instead of 7 minutes (i.e., has a greater slope between the 12-minute mark and the 15-minute mark to "catch up" to the originally generated solvent gradient 364). As a result, the gradient hold button 416 can function as a manual override of the originally generated solvent gradient 364.

The tube advance button 418 can be pressed to advance the fraction collector 124, and particularly, the carriage 196 of the fraction collector 124 to the next collection vessel 126. This can be used for a variety of purposes. In some embodiments, the tube advance button 418 can be used as a safety measure if the user observes that a collection vessel 126 may be about to overflow, for example, if the collection vessel 126 was not completely empty when it began to be filled. In some embodiments, the tube advance button 418 can be pressed when the user observes what appears to be a new peak in the chromatogram 370, but which is not being detected as a new peak by the fraction collecting software, based on the collection mode and parameters that have been set. In such embodiments, the user can press the tube advance button 418 to begin collecting the new peak in a new collection vessel 126 to, essentially, manually separate the fractions of the sample 101.

The drain button 420 can be pressed to tell the fraction collector 124, and particularly, the divert valve 184 of the fraction collector 124 to send all fractions of the sample 101 out the first outlet 188 to waste. When the drain button 420 is pressed, the fraction collecting software is overridden, and no fractions are collected until the drain button 420 is pressed a second time. The drain button 420 can be pressed a second time to resume collecting fractions according to the settings in the fraction collecting software.

The LCD screen 134 on the touchpad 132 can be used to display current settings in the chromatography process relating to programming a run, priming the chromatography system 100, and/or running the chromatography system 100.

In operation, a user would power on the chromatography system 100 and would open the chromatography programming software, and particularly, the wizard program 220. The wizard program 220 would default to the 'General' screen 222, and the user would have the option of creating a new method file or loading an existing method file, as described above. The user can then select the type of cartridge 120 and solvents 115 to be used for the chromatography run, and enter any notes into the text field 244 of the 'Description' field 242. The user can change various system options, as described above, by selecting the 'System Options . . . ' button 270, and the user can prime one or both of the pump heads 158a, 158b and enter or select the flow rate and volume of the solvents 115 by selecting the 'Prime Pumps . . . ' button 258. The user can enter a sample identification into the 'Sample ID' field 229, or the user can enable auto-sequencing by selecting the sample ID wizard button 208, as described above with respect to FIG. 8B.

The user can then advance to the 'Detection' screen 224 by clicking on the 'Detection' tab at the top of the main window 221 of the wizard program 200. The 'Detection' screen 224 includes default settings, and many users will not make adjustments to the 'Detection' screen 224, except to modify the 'Rack Settings' field 308. However, any of the other fields in the 'Detection' screen 224 can be modified, as described above.

The user can then advance to the 'Pump' screen 226 by clicking on the 'Pump' tab at the top of the main window 221. The user can generate a solvent gradient 364 by adding rows to the solvent gradient spreadsheet 350, based on the sample 101 of interest. The user can then modify the 'Equilibration' parameters in the 'Equilibration' field 346 or the 'Purification' flow rate in the 'Purification' field 356, as described above. The user can also make note of the required amount of solvents 115, based on the display in the required solvent volume field 358.

The user can then advance to the 'Chromatogram' screen 228 by clicking on the 'Chromatogram' screen 228 to run and monitor the chromatography run. The 'Chromatogram' screen 228 can also be used to view previous results. If the user wishes to begin a chromatography run, he/she can select the 'Run' button 230 located in the static region 227 of the main window 221. As mentioned above, unless the 'Run Summary' window option has been turned off, after the user has selected the 'Run' button 230, the 'Run Summary' window 290 will open and allow the user to review the run summary and abort beginning the run by selecting the 'Abort' button 294, if desired, or continue the chromatography process by selecting the 'Continue' button 292. If the 'Continue' button 292 is selected, the chromatography system 100 will begin equilibrating the cartridge 120, as shown in FIG. 19 and described above, which can be skipped or paused by selecting the 'Skip' button 392 or the 'Pause' button 394, respectively. In addition, the 'Run' button 230 has now changed to the 'Pause' button 295, and the 'Pause' button 295 can be used to pause and restart the run or pause and abort the run.

After the cartridge 120 has been equilibrated, or after equilibration has been skipped, the 'Inject Sample' window 396 will open, and user can introduce the sample 101 into the chromatography system 100 in two ways, as described above. After the sample 101 has been injected, the user can select the 'Resume' button 404 to resume the chromatography run, or the 'Abort' button 406 to abort the chromatography run. If the user selects the 'Resume' button 404, the pump assembly 110 will move the solvents 115 from the containers 125 to the mixing valve 113 to be mixed according to the solvent gradient 364 specified to form the mobile phase of the chromatography system 100, and pumped by the pump 114 through the fluid path 112 and to the cartridge 120. The sample 101 will be moved through the cartridge 120 with the mobile phase of the chromatography system 100, passed the stationary phase 121. The sample 101 will be separated into fractions based on the relative affinities of the fractions in the sample 101 for the mobile phase and the stationary phase 121. The fractions will then be directed from the outlet 123 of the cartridge 120 to the inlet 174 of the flow cell 170 of the detector 122, where the fractions of the sample 101 will be identified and distinguished.

Based on the reading from the detector 122, a chromatogram 370 displaying the absorbance of radiation of each fraction will be created in the 'Chromatogram' screen 228 of the wizard program 220 of the graphical user interface 106. Based on the parameters and collection mode chosen of the fraction collecting software, the fraction collecting software will determine when one fraction ends and a new fraction begins. As fractions pass through the flow cell 170, and out the outlet 176 of the flow cell 170, the fractions are directed to the divert valve 184 of the fraction collector 124, and either sent to waste via the first outlet 188, or sent out of the nozzle 198 to a collection vessel via the second outlet 190, depending on the signals received from the controller 104, based on the fraction collecting software.

When a new fraction is detected, the arm and/or the carriage 196 of the fraction collector 124 will index to a new collection vessel 126 to collect the newly identified fraction in a new collection vessel 126. The fraction collector 124 will also index to a new collection vessel 126 when one collection vessel 126 is almost full, based on the data stored in the chromatography programming software regarding the type of collection vessel 126 and collection vessel stand 128 being used. As shown in FIG. 17, the graphic rack display 374 in the 'Chromatogram' screen 288 will show the relationship (i.e., fraction mapping) between the contents of the collection vessels 126 and the peaks of the chromatogram 370.

Various features and aspects of the invention are set forth in the following claims.

What is claimed is:

1. A method for analyzing a sample of interest using chromatography, the sample including fractions, the method comprising:
providing a fluid path through which the sample moves during a chromatography run, the chromatography run having a first expiration time;
separating the fractions of the sample to allow the fractions of the sample to move through the fluid path at different rates;
moving the fractions of the sample along the fluid path;
selectively collecting fractions of the sample according to fraction collecting software, the act of selectively collecting fractions including
detecting a positive change in slope corresponding to a peak indicative of a fraction, calculating a volume of fluid in the fluid path prior to the peak as a result of detecting the positive change in slope, and collecting a delay volume in the fluid path; and extending the chromatography run to a second expiration time when the first expiration time occurs during collection of a fraction, the second expiration time being later than the first expiration time.

2. The method of claim 1, wherein the second expiration time occurs when the fraction collecting software determines that collection of the fraction is complete.

3. The method of claim 1, wherein extending the chromatography run to a second expiration time occurs automatically when the fraction collecting software determines that collection of the fraction is not complete at the first expiration time.

4. The method of claim 1, further comprising detecting the fractions of the sample based on each fraction's electromagnetic radiation absorbance.

5. The method of claim 1, further comprising creating a chromatogram representative of the fractions of the sample, and wherein selectively collecting fractions of the sample according to fraction collecting software includes selectively collecting fractions of the sample based on at least one of the slope of the chromatogram, the value of the chromatogram, the slope and the value of the chromatogram, and the slope or the value of the chromatogram.

6. The method of claim 1, wherein separating the fractions of the sample includes moving a mobile phase comprising the sample through a chromatography cartridge comprising a stationary phase.

* * * * *